United States Patent
Kumar et al.

(10) Patent No.: US 12,220,667 B2
(45) Date of Patent: Feb. 11, 2025

(54) ORGANIC SOLVENT METHOD FOR PREPARING MEMBRANE PROTEIN BASED NANOSHEETS AND MEMBRANES BASED ON NANOSHEETS

(71) Applicant: THE PENN STATE RESEARCH FOUNDATION, University Park, PA (US)

(72) Inventors: Manish Kumar, State College, PA (US); Tingwei Ren, State College, PA (US); Woochul Song, State College, PA (US); Yu-Ming Tu, State College, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 198 days.

(21) Appl. No.: 17/645,380

(22) Filed: Dec. 21, 2021

(65) Prior Publication Data
US 2022/0118408 A1    Apr. 21, 2022

Related U.S. Application Data

(62) Division of application No. 16/414,517, filed on May 16, 2019, now Pat. No. 11,235,286.
(Continued)

(51) Int. Cl.
*B01D 67/00* (2006.01)
*B01D 69/14* (2006.01)
(Continued)

(52) U.S. Cl.
CPC ..... *B01D 67/00091* (2022.08); *B01D 69/144* (2013.01); *B01D 71/24* (2013.01);
(Continued)

(58) Field of Classification Search
CPC .... B01D 61/027; B01D 67/009; B01D 69/10; B01D 69/106; B01D 69/144; B01D 71/24; B01D 71/52; B01D 71/56; B01D 71/80
(Continued)

(56) References Cited

U.S. PATENT DOCUMENTS 9,738,683 B2    8/2017   McKee et al.
9,783,678 B2   10/2017   Kumar et al.
(Continued)

FOREIGN PATENT DOCUMENTS

CN    101862609 A  * 10/2010   ......... B01D 67/0006

OTHER PUBLICATIONS

Schlesinger et al., "Evaluation of alkali resistant nanofiltration membranes for the separation of hemicellulose from concentrated alkaline process liquors", vol. 192, pp. 303-314, 2006.
(Continued)

*Primary Examiner* — Tri V Nguyen
(74) *Attorney, Agent, or Firm* — McKee, Voorhees & Sease, PLC

(57) ABSTRACT

The present disclosure describes compositions and methods for preparing membrane protein nanosheets and two-dimensional crystals. In particular, the methods employ a solvent. A mixture of a polymer and a membrane protein is solubilized in the solvent, applied to a substrate, and subsequently dried to form the nanosheet or two-dimensional crystal. Applicants have surprisingly found that the membrane proteins maintain their structure when exposed to solvents during the short processing time utilized.

17 Claims, 13 Drawing Sheets

Related U.S. Application Data

(60) Provisional application No. 62/672,309, filed on May 16, 2018.

(51) Int. Cl.

| | | |
|---|---|---|
| *B01D 71/24* | (2006.01) | |
| *B01D 71/26* | (2006.01) | |
| *B01D 71/52* | (2006.01) | |
| *B01D 71/56* | (2006.01) | |
| *B01D 71/80* | (2006.01) | |
| *C07K 14/245* | (2006.01) | |
| *C07K 14/31* | (2006.01) | |
| *C07K 14/47* | (2006.01) | |

(52) U.S. Cl.
CPC ........ *B01D 71/261* (2022.08); *B01D 71/5211* (2022.08); *B01D 71/56* (2013.01); *B01D 71/80* (2013.01); *C07K 14/245* (2013.01); *C07K 14/31* (2013.01); *C07K 14/47* (2013.01)

(58) Field of Classification Search
USPC ..................................................... 428/304.4
See application file for complete search history.

(56) References Cited

U.S. PATENT DOCUMENTS

| 10,538,632 | B1* | 1/2020 | Kaehr ................. C12N 5/0693 |
| --- | --- | --- | --- |
| 10,688,442 | B2 | 6/2020 | Mauter et al. |
| 2006/0027455 | A1 | 2/2006 | Patton et al. |
| 2007/0187243 | A1 | 8/2007 | Patton et al. |
| 2009/0007555 | A1 | 1/2009 | Jensen |
| 2010/0270233 | A1 | 10/2010 | Kim et al. |
| 2011/0046074 | A1 | 2/2011 | Kumar et al. |
| 2012/0025414 | A1 | 2/2012 | Schmidt et al. |
| 2012/0129270 | A1 | 5/2012 | Nallani et al. |
| 2014/0051785 | A1 | 2/2014 | Kumar et al. |
| 2014/0332468 | A1 | 11/2014 | Tang et al. |
| 2015/0136690 | A1* | 5/2015 | Xie ........................ B01D 71/06 427/244 |
| 2015/0273407 | A1 | 10/2015 | Gil et al. |
| 2016/0151747 | A1* | 6/2016 | Jungbauer ............ B01D 71/601 210/500.33 |
| 2017/0176449 | A1 | 6/2017 | Keyes et al. |
| 2020/0206136 | A1 | 7/2020 | Prud'Homme et al. |
| 2021/0008507 | A1 | 1/2021 | Dorin et al. |

OTHER PUBLICATIONS

Schneider et al., "Columnar Self-Assemblies of Triarylamines as Scaffolds for Artificial Biomimetic Channels for Ion and for Water Transport", J. Am. Chem. Soc., vol. 139, pp. 3721-3727, Feb. 16, 2017.
Shen et al., "Highly permeable artificial water channels that can self-assemble into two-dimensional arrays", PNAS, vol. 112, No. 32, pp. 9810-9815, Aug. 11, 2015.
Shen et al., "Biomimetic membranes: A review", Journal of Membrane Science, vol. 454, pp. 359-381, 2014.
Signorell et al., "Controlled 2D crystallization of membrane proteins using methyl-ß-cyclodextrin", Journal of Structural Biology, vol. 157, pp. 321-328, 2007.
Song et al., "Hierarchical Optimization of High-Performance Biomimetic and Bioinspired Membranes", Langmuir, vol. 35, pp. 589-607, Dec. 21, 2018.
Song et al., Design Considerations for Artificial Water Channel-Based Membranes, Annu. Rev. Mater. Res., vol. 48, pp. 57-82, Mar. 23, 2018.
Tamm et al., "Structure and Assembly of ß-Barrel Membrane Proteins", The Journal of Biological Chemistry, vol. 276, No. 35. pp. 32399-32402, Issue of Aug. 31, 2001.
Tang et al., "Desalination by biomimetic aquaporin membranes: Review of status and prospects", Desalination, vol. 308, pp. 34-40, 2013.
Tang et al., "Tubular ceramic-based multilayer separation membranes using spray layer-by-layer assembly", Polym. Chem., vol. 4, pp. 5621-5628, Jul. 8, 2013.
Thebo et al., "Highly stable graphene-oxide-based membranes with superior permeability", Nature Communications, 9 pages, 2018.
Tunuguntla et al., "Enhanced water permeability and tunable ion selectivity in subnanometer carbon nanotube porins", Science, vol. 357, pp. 792-796, Aug. 25, 2017.
Wang et al., "Layer-by-Layer Assembly of Aquaporin Z-Incorporated Biomimetic Membranes for Water Purification", Environ. Sci. Technol., vol. 49, pp. 3761-3768, Mar. 2, 2015.
Werber et al., "Materials for next-generation desalination and water purification membranes", Nature Reviews, 16 pages, Apr. 5, 2016.
White et al., "Membrane Protein Folding and Stability: Physical Principles", Annu. Rev. Biophys. Biomol. Struct., vol. 28, pp. 319-365 1999.
Wimley, William, "The versatile ß-barrel membrane protein", Current Opinion in Structural Biology, vol. 13, pp. 404-411, 2003.
Won et al., "Cryogenic Transmission Electron Microscopy (Cryo-TEM) of Micelles and Vesicles Formed in Water by Poly(ethylene oxide)-Based Block Copolymers", J. Phys. Chem., vol. 106, pp. 3354-3364, Jan. 3, 2002.
Wong et al., "Single molecule measurements of channel proteins incorporated into biomimetic polymer membranes", Nanotechnology, vol. 17, pp. 3710-3717, Jun. 12, 2006.
Xu et al., "Subnanometer Porous Thin Films by the Co-assembly of Nanotube Subunits and Block Copolymers", ACS Nano, vol. 5, No. 2, pp. 1376-1384, 2011.
Xu et al., "A wide range and high resolution one-filtration molecular weight cut-off method for aqueous based hanofiltration and ultrafiltration membranes", Journal of Membranes Science, vol. 525, pp. 304-311 2017.
Xue et al., "Pillararenes, A New Class of Macrocycles for Supramolecular Chemistry", Accounts of Chemical Research, vol. 45, No. 8, pp. 1294-1308, 2012.
Zeidel et al., "Reconstitution of Functional Water Channels in Liposomes Containing Purified Red Cell CHIP28 Protein", Biochemistry, vol. 31, pp. 7436-7440, Jun. 16, 1992.
Zhang et al., "Vesicular perylene dye nanocapsules as supramolecular flourescent pH sensor systems", Nature Chemistry, vol. 1, pp. 623-629, Nov. 2008.
Zhao et al., "Selective anion exchange with nanogated isoreticular positive metal-organic frameworks", Nature Communications, 10 pages, Aug. 16, 2013.
Zhou et al., "Self-assembling subnanometer pores with unusual mass-transport properties", Nature Communications, 9 pages, Jul. 17, 2012.
Zhu et al., "Collective Diffusion Model for Water Permeation through Microscopic Channels", Physcial Review Letters, 4 pages, Nov. 24, 2004.
Zirehpour et al., "Unique membrane process integration for olive oil mill wastewater purification", Separation and Purification Technology, vol. 96, pp. 124-131, May 21, 2012.
Zydney, Andrew, "Stagnant film model for concentration polarization in membrane systems", Journal of Membrane Science, vol. 130, pp. 275-281, 1997.
Feroz et al., "Can Fibrous Mats Outperform Current Ultrafiltration and Microfiltration Membranes", Ind. Eng. Chem. Res., vol. 56, pp. 10438-10447, Aug. 15, 2017.
Fei et al., "A Synthetic Zwitterionic Water Channel: Characterization in the Solid State by X-ray Crystallography and NMR Spectroscopy", Angew. Chem. Int. Ed., vol. 44, pp. 5720-5725, 2005.
Le Duc et al., "Imidazole-Quartet Water and Proton Dipolar Channels", Angew. Chem. Int. Ed., vol. 50, pp. 11366-11372, 2011.
Zhao et al., "Proton Gradient-Induced Water Transport Mediated by Water Wires Inside Narrow Aquapores of Aquafoldamer Molecules", J. Am. Chem. Soc., vol. 136, pp. 14270-14276, Sep. 16, 2014.
Barboiu, Mihail, "Artificial water channels—incipient innovative developments", Chem. Commun., vol. 52, pp. 5657-5665, Mar. 23, 2016.

(56) References Cited

OTHER PUBLICATIONS

Tunuguntla et al., "Ultrafast proton transport in sub-1-nm diameter carbon nanotube porins", Nature Nanotechnology, vol. 11, 8 pages, Jul. 2016.
Antonietti et al., "Vesicles and Liposomes: A Self-Assembly Principle Beyond Lipids", Adv. Mater., vol. 15, No. 16, pp. 1323-1333, Aug. 2015.
Discher et al., "Polymersomes Tough Vesicles Made from Diblock Copolymers", Science, vol. 284, pp. 1143-1147, May 14, 1999.
Zhang et al., "Natural channel protein inserts and functions in a completely artificial, solid-supported bilayer membrane", Scientific Reports, 7 pages, Jul. 12, 2013.
Horner et al., "Comment on " Enhanced water permeability and tunable ion selectivity in subnanometer carbon nanotube porins, Science, vol. 359, 3 pages Mar. 30, 2018.
Tunuguntla et al., "Response to Comments on Enhanced water permeability and turnable ion selectivity in subnanometer carbon nanotube porins", Science, vol. 359, 3 pages Mar. 30, 2018.
Niedzwiecki et al., "Inspection of the Engineered FhuA ΔC/Δ4L Protein Nanopore by Polymer Exclusion", Biophysical Journal, vol. 103, pp. 2115-2124, Nov. 2012.
Haltia et al., "Forces and factors that contribute to the structural stability of membrane proteins", Biochimica et Biophysica Acta, vol. 1228, pp. 1-27, Oct. 17, 1994.
Jegal et al., "Factors Affecting the Interfacial Polymerization of Polyamide Active Layers for the Formation of Polyamide Composite Membranes", Journal of Applied Polymer Science, vol. 86, pp. 2781-2787, Mar. 14, 2002.
Shen et al., "Achieving high permeability and enhanced selectivity for Angstrom-scale separations using artificial water channel membranes", Nature Communications, 11 pages, 2018.
Wallace et al., "Differential Absorption Flattening Optical Effects Are Significant in the Circular Dichroism Spectra of Large Membrane Fragments", Biochemistry, vol. 26, pp. 65-70, Aug. 1, 1986.
Kumar et al., High-Density Reconstitution of Functional Water Channels into Vesicular and Planar Block Copolymer Membranes, J. Am. Chem. Soc., vol. 134, pp. 18631-18637, Oct. 22, 2012.
Agre, Peter, Aquaporin Water Channels (Nobel Lecture), Angew. Chem. Int. Ed., vol. 43, pp. 4278-4290, 2004.
Azais et al., "Nanofiltration for wastewater reuse: Counteractive effects of fouling and matrice on the rejection of pharmaceutical active compounds", Separation and Purification Technology, vol. 133, pp. 313-327, Jul. 4, 2014.
Baek et al., "High Performance and antifouling vertically aligned carbon nanotube membrane for water purification", Journal of Membrane Science, vol. 460, pp. 171-177, Feb. 25, 2014.
Barden et al., "Parameterization and atomistic simulations of biomimetic membranes", Faraday Discuss., vol. 209, pp. 161-178, Apr. 13, 2018.
Belegrinou et al., "Biomimetic supported membranes from amphiphilic block copolymers", Soft Matter, vol. 6, pp. 179-186, 2010.
Bellona et al., "The role of membrane surface charge and solute physico-chemical properties in the rejection of organic acids by NF membranes", Journal of Membrane Science, vol. 249, pp. 227-234, 2005.
Bermudez et al., "Molecular Weight Dependence of Polymersome Membrane Structure, Elasticity, and Stability", Macromolecules, vol. 35, pp. 8203-8208, Jul. 26, 2002.
Bezrukov et al., "Dynamics and Free Energy of Polymers Partitioning into a Nanoscale Pore", Macromolecules, vol. 29, pp. 8517-8522, Sep. 20, 1996.
Bhakdi et al., "Alpha-Toxin in *Staphylococcus aureus*", Microbiological Reviews, vol. 55, No. 4, pp. 733-751, Dec. 1991.
Bhakdi et al., "Correlation Between Toxin Binding and Hemolytic Activity in Membrane Damage by *Staphylococcal* α-Toxin", Infection and Immunity, pp. 318-323, Nov. 1984.
Biyani et al. "Focus: The interface between data collection and data processing in cryo-EM", Journal of Structural Biology, vol. 198, pp. 124-133, Mar. 20, 2017.

Blanazs et al., "Self-Assembled Block Copolymer Aggregates: From Micelles to Vesicles and their Biological Applications", Macromol. Rapid Commun., vol. 30, pp. 267-277, 2009.
Boussu et al., "Characterization of commercial nanofiltration membranes and comparison with self-made polyethersulfone membranes", Desalination, vol. 191, pp. 245-253, 2006.
Boussu et al., "Characterization of polymeric nanofiltration membranes for systematic analysis of membrane performance", Journal of Membrane Science, vol. 278, pp. 418-427, 2006.
Bowie, James, "Solving the membrane protein folding problem", Nature, vol. 438, pp. 581-589, Dec. 1, 2005.
Braeken et al., "Transport mechanisms of dissolved organic compounds in aqueous solutions during nanofiltration", Journal of Membrane Science, vol. 279, pp. 331-319 2006.
Bulheller et al., "DichroCalc—circular and linear dichroism online", Bioinformatics, vol. 25, No. 4, pp. 539-540, Jan. 5, 2009.
Caus et al., "The use of integrated countercurrent nanofiltration cascades for advanced separations", J Chem Technol Biotechnol., vol. 84, pp. 391-398, 2009.
Cerritelli et al., "PEG-SS-PPS: Reduction-Sensitive Disulfide Block Copolymer Vesicles for Intracellular Drug Delivery", Biomacromolecules, vol. 8, pp. 1966-1972, Apr. 3, 2007.
Chowdhury et al., "PoreDesigner for tuning solute selectivity in a robust and highly permeable outer membrane bore" Nature Communicaitons, 11 pages, 2018.
Cornelis et al., "Nanaofiltration of Nonionic Surfactants: Effect of the Molecular Weight Cutoff and Contact Angle on Flux Behavior", Ind. Eng. Chem. Res., vol. 44, pp. 7652-7658, 2005.
Cowan et al., "Crystal structures explain functional properties of two *E. coli* porins", Nature, vol. 358, pp. 727-733, Aug. 27, 1992.
De Groot et al., "Water Permeation Across Biological Membranes: Mechanism and Dynamics of Aquaporin-1 and GlpF", Science, vol. 294, pp. 2353-2357, Dec. 14, 2001.
Dean III et al., "Modeling healthy male white matter and myelin development: 3 through 60 months of age", NeuroImage, vol. 84, pp. 742-752, 2014.
Discher et al., "Polymer Vesicles", Science, vol. 297, No. 5583, pp. 967-973 Aug. 9, 2002.
Dolder et al., "The micelle to vesicle transition of lipids and detergents in the presence of a membrane protein: towards a rationale of 2D crystallization", FEBS Letters, vol. 382, pp. 203-208, Feb. 5, 1996.
Dorset et al., "Two-dimensional Crystal Packing of Matrix Porin, A Channel Forming Protein in *Escherichia coli* Outer Membranes", J. Mol. Biol., vol. 165, pp. 701-710, 1983.
Duong et al., Planar biomimetic aquaporin-incorporated triblock copolymer membranes on porous alumina supports for nanofiltration, Journal of Membrane Science, vol. 409-410, pp. 34-43, Mar. 1, 2012.
Efremov et al., "Structure of *Escherichia coli* OmpF porin from lipidic mesophase", Journal of Structural Biology, vol. 178, pp. 311-318, Mar. 20, 2012.
Feroz et al., "Concentrating Membrane Proteins Using Ultrafiltration Without Concentrating Detergents", Biotechnology and Bioengineering, vol. 113, No. 10, pp. 2122-2130 Oct. 2016.
Ferro et al., "Organic solvent extraction as a versatile procedure to identify hydrophobic chloroplast membrane proteins", Electrophoresis, vol. 21, pp. 3517-3526, 2000.
Fornasiero et al., "Ion exclusion by sub-2-nm carbon nanotube pores", PNAS, vol. 105, No. 45, pp. 17250-17255, Nov. 11, 2008.
Freeman, Benny, "Basis of Permeability/Selectivity Tradeoff relations in Polymeric Gas Separation Membranes", Macromolecules, vol. 32, pp. 375-380, 1999.
Fujioka et al., "Nanofiltration of trace organic chemicals: A comparison between ceramic and polymeric membranes". Separation and Purification Technology, vol. 136, pp. 258-264, Aug. 30, 2014.
Garner et al., "Modification of the Optoelectronic Properties of Membranes via Insertion of Amphiphilic Phenylenevinylene Oligoelectrolytes", J. Am. Chem. Soc., vol. 132, pp. 10042-10052, Feb. 24, 2010.
Ge et al., "Vertically-aligned carbon nanotube membranes for hydrogen separation", RSC Advances, vol. 2, pp. 5329-5336, Mar. 27, 2012.

(56) References Cited

OTHER PUBLICATIONS

Geise et al., "Water permeability and water/salt selectivity tradeoff in polymers for desalination", Journal of Membrane Science, vol. 369, pp. 130-138, 2011.

Geng et al., "Stochastic transport through carbon nanotubes in lipid bilayers and live cell membranes", Nature, vol. 514, 17 pages. Oct. 30, 2014.

Gessmann et al., "Improving the Resistance of a Eukaryotic B-Barrel Protein to Thermal and Chemical Perturbations", J. Mol. Biol., vol. 413, pp. 150-161, Jul. 23, 2011.

Gouaux et al., "Subunit stoichiometry of staphylococcal α-hemolysin in crystals and on membranes: A heptameric transmembrane pore", Proc. Natl. Acad. Sci. USA, vol. 91, p. 12828-12831, Dec. 1994.

Grzelakowski et al., "A framework for accurate evaluation of the promise of aquaporin based biomimetic membranes", Journal of Membrane Science, vol. 479, pp. 223-231, Jan. 10, 2015.

Grzelakowski et al., "Terminal groups control self-assembly of amphiphilic block copolymers in solution", Nanoscale, vol. 8, pp. 6674-6683, Feb. 23, 2016.

Habel et al., "Selecting analytical tools for characterization of polymersomes in aqueous solution", RSC Advances 5, pp. 79924-79946, 2015.

Hasler et al., "2D Crystallization of Membrane Proteins: Rationales and Examples", Journal of Structural Biology, vol. 121, pp. 162-171, Jan. 5, 1998.

Helix-Nielsen, Claus, "Biomimetic Membranes as a Technology Platform: Challenges and Opportunties", Membranes, vol. 8, No. 44, 16 pages, Jul. 17, 2018.

Hinds et al., "Aligned Multiwalled Carbon Nanotube Membranes", Science, vol. 303, pp. 62-65, Jan. 2, 2004.

Holt et al., "Fast Mass Transport Through Sub-2-Nanometer Carbon Nanotubes", Science, vol. 312, No. 5776, pp. 1034-1037 May 19, 2006.

Holt et al., "Fabrication of a Carbon Nanotube-Embedded Silicon Nitride Membrane for Studies of Nanometer-Scale Mass Transport", Nanoletters, 20 pages, Aug. 27, 2004.

Hu et al., "Enabling Graphene Oxide Nanosheets as Water Separation Membranes", Environ. Sci. Technol., vol. 47, pp. 3715-3723, Mar. 14, 2013.

Saboe et al., "Role of Pore-Lining Residues in Defining the Rate of Water Conduction by Aquaporin-0", Biophysical Journal, vol. 112, pp. 953-965, Mar. 14, 2017.

Hu et al., "Single-Molecular Artificial Transmembrane Water Channels", J. Am. Chem. Soc., vol. 134, pp. 8384-8387, May 10, 2012.

Huang et al., "Graphene oxide nanosheet: an emerging star material for novel separation membranes", J Mater. Chem., vol. 2, pp. 13772-13782, Jun. 13, 2014.

Humphrey et al., "VMD: Visual Molecular Dynamics", Journal of Molecular Graphics, vol. 14, pp. 33-38, 1996.

Itel et al., "Dynamics of Membrane Proteins within Synthetic Polymer Membranes with Large Hydrophobic Mismatch", Nano Lett., vol. 15, pp. 3871-3878, May 27, 2015.

Jap et al., "2D crystallization: from art to science, Ultramicroscopy, vol. 46, pp. 45-84, Jul. 1992.

Jin et al., "Highly stable and self-repairing membrane-mimetic 2D nanomaterials assembled from lipid-like peptoids", Nature Communications, 8 pages, Jul. 12, 2016.

Kale et al., "NAMD2: Greater Scalability for Parallel Molecular Dynamics", Journal of Computational Physics, vol. 151, pp. 283-312, 1999.

Kaucher et al., "Selective Transport of Water Mediated by Porous Dendritic Dipeptides", J. Am. Chem. Soc., vol. 129, pp. 11698-11699, Aug. 12, 2007.

Kelewou et al., "Salts retention by nanofiltration membranes: Physicochemical and hydrodynamic approaches and modeling", Desalination, vol. 277, pp. 106-112, Apr. 3, 2011.

Kelly et al., "How to study proteins by circular dichroism", Biochimica et Biophysica Acta, vol. 1751, pp. 119-139, Jun. 8, 2005.

Kim et al., "CHARMM-GUI Ligand Reader and Modeler for CHARMM Force Field Generation of Small Molecules", Journal of Computational Chemistry, vol. 38, pp. 1879-1886, 2017.

Kita-Tokarczyk et al., "Block copolymer vesicles—using concepts from polymer chemistry to mimic biomembranes", Polymer, vol. 46, pp. 3540-3563, Feb. 14, 2005.

Klara et al., "Magnetically Directed Two-Dimensional Crystallization of OmpF Membrane Proteins in Block Copolymers", J. Am. Chem. Soc., vol. 138, pp. 28-31, 2016.

Kleffel et al., "Secondary structure of a channel-forming protein: porin from *E. coli* outer membranes", The EMBO Journal, vol. 4, No. 6, pp. 1589-1592, 1985.

Kocsis et al., "Artificial water channels—deconvolution of natural Aquaporins through synthetic design", Clean Water, 11 pages, Apr. 12, 2018.

Kowal et al., "Planar Biomimetic Membranes Based on Amphiphilic Block Copolymers", ACS Macro Lett., vol. 3, pp. 59-63, Dec. 27, 2014.

Krieg et al., "Salt rejection in nanofiltration for single and binary salt mixtures in view of sulphate removal", Desalination, vol. 171, pp. 205-215, May 5, 2004.

Kumar et al., "Highly permeable polymeric membranes based on the incorporation of the functional water channel protein Aquaporin Z", PNAS, vol. 104, No. 52, pp. 20719-20724, Dec. 26, 2007.

Lang et al., "Creating cross-linked lamellar block copolymer supporting layers for biomimetic membranes", Faraday Discuss., vol. 209, pp. 179-191, Feb. 26, 2018.

Latimer et al., "Light Scattering at Various Angles: Theoretical Predications of the Effects of Particle Volume Changes", Biophysical Journal, vol. 12, pp. 764-773, 1972.

Lee, A.G., "Lipid-protein interactions in biological membranes: a structural perspective", Biochimica et Biophysica Acta, vol. 1612, pp. 1-40, Feb. 14, 2003.

Licsandru et al., "Salt-Excluding Artificial Water Channels Exhibiting Enhanced Dipolar Water and Proton Translocation", J. Am. Chem. Soc., vol. 138, pp. 5403-5409, Apr. 10, 2016.

Liu et al., "Two-Dimensional-Material Membranes: A New Family of High-Performance Separation Membranes", Angew. Chem. Int. Ed., vol. 55, pp. 13384-13397, 2016.

Luo et al., "Separation of phenolic acids from monosaccharides by low-pressure nanofiltration integrated with laccase pre-treatments", Journal of Membrane Science, vol. 482, pp. 83-91, Feb. 14, 2015.

MacCallum et al., "Distribution of Amino Acids in a Lipid Bilayer from Computer Simulations", Biophysical Journal, vol. 94, pp. 3393-3404, May 2008.

Mackerell et al., "All-Atom Empirical Potential for Molecular Modeling and Dynamics Studies of Proteins", J. Phys. Chem., vol. 102, pp. 3586-3616, Feb. 6, 1998.

Mai et al., "Self-assembly of block copolymers", Chem. Soc. Rev., vol. 41, pp. 5969-5985, Apr. 2, 2012.

Manzo et al., "Enhanced Amphiphilic Profile of a Short ß-Stranded Peptide Improves its Antimicrobial Activity", PLOS One, 19 pages, Jan. 24, 2015.

Mehta et al., "Permeability and selectivity analysis for ultrafiltration membranes", Journal of Membrane Science, vol. 249, pp. 245-249, 2005.

Mi, Baoxia, "Graphene Oxide Membranes for Ionic and Molecular Sieving", Science, vol. 343, 4 pages, Feb. 14, 2014.

Mo et al., "Cation-dependent structural instability of graphene oxide membranes and its effect on membrane separation performance", Desalination, vol. 399, pp. 40-46, Aug. 7, 2016.

Mohammad et al., "Redesign of a Plugged ß-Barrel Membrane Protein", The Journal of Biological Chemical, vol. 286, No. 10, pp. 8000-8013, Mar. 11, 2011.

Mohammad et al., "Fabrication of Vertically Aligned CNT Composite for Membrane Applications Using Chemical Vapor Deposition through In Situ Polymerization", Journal of Nanomaterials, vol. 2013, Article ID 713583, 5 pages, Jun. 23, 2013.

Moon et al., "Side-chain hydrophobicity scale derived from transmembrane protein folding into lipid bilayers", PNAS, vol. 108, No. 25, pp. 10174-10177, Jun. 21, 2011.

Nikaido, H., "Porins and specific channels of bacterial outer membranes", Molecular Microbiology, vol. 6(4), pp. 435-442, 1992.

(56) References Cited

OTHER PUBLICATIONS

Nikaido et al., "Transport Proteins in Bacteria: Common Themes in Their Design", Science, vol. 258, No. 5084, pp. 936-942, Nov. 6, 1992.

Palivan et al., "Bioinspired polymer vesicles and membranes for biological and medical applications", Chem. Soc. Rev., vol. 45, pp. 377-411, 2016.

Panganiban et al., "Random heteropolymers preserve protein function in foreign environments", Science, vol. 359, pp. 1239-1243, Mar. 16, 2018.

Park et al., "Maximizing the right stuff: The trade-off between membrane permeability and selectivity", Science, vol. 356, 12 p. Jun. 16, 2017.

Peinemann et al., "Asymmetric superstructure formed in a block copolymer via phase separation", Nature Materials, vol. 6, pp. 992-996, Dec. 2007.

Peng et al., "Metal-organic framework nanosheets as building blocks for molecular sieving membranes", Science, vol. 346, Issue 6215, 5 pages, Dec. 12, 2014.

Plakas et al., "A study of selected herbicides retention by nanofiltration membranes—The role of organic fouling", Journal of Membrane Science, vol. 284, pp. 291-300, Jul. 27, 2006.

Rajesh et al., Mixed Mosaic Membranes Prepared by Layer-by-Layer Assembly for Ionic Separations, vol. 8, No. 12, pp. 12338-12345, Dec. 3, 2014.

Rakhmatullina et al., "Solid-Supported Block Copolymer Membranes through Interfacial Adsorption of Charged Block Copolymer Vesicles", Langmuir, vol. 24, pp. 6254-6261, Mar. 25, 2008.

Rathee et al., "A coarse-grained thermodynamic model for the predictive engineering of valence-selective membranes", Mol. Syst. Des. Eng., vol. 1, pp. 301-312, Jul. 28, 2016.

Ren et al., "Membrane Protein Insertion into and Compatibility with Biomimetic Membranes", Adv. Biosys., vol. 1, 10 pages, 2017.

Robeson, Lloyd, "The upper bound revisited", Journal of Membrane Science, vol. 320, pp. 390-400, Apr. 14, 2008.

Robeson, Lloyd, "Correlation of separation factor versus permeability for polymeric membranes", Journal of Membrane Science, vol. 62, pp. 165-185, Feb. 13, 1991.

Rohani et al., "A refined one-filtration method for aqueous based nanofiltration and ultrafiltration membrane molecular weight cut-off determination using polyethylene glycols", Journal of Membrane Science, vol. 382, pp. 278-290, Aug. 10, 2011.

Abraham et al., "Tunable sieving of ions using graphene oxide membranes", Nature Nanotechnology, vol. 12, 7 pages, Jun. 2017.

\* cited by examiner

ORGANIC SOLVENT METHOD FOR PREPARING MEMBRANE PROTEIN BASED NANOSHEETS AND MEMBRANES BASED ON NANOSHEETS

CROSS REFERENCE TO RELATED APPLICATIONS

This is a divisional application of U.S. Ser. No. 16/414,517, filed May 16, 2019, which claims priority to provisional application U.S. Ser. No. 62/672,309, filed May 16, 2018, which are incorporated herein by reference in their entirety.

GOVERNMENT SPONSORSHIP

This invention was made with government support under Grant Nos. CBET1512099 and CBET1552571 awarded by the National Science Foundation. The Government has certain rights in the invention.

TECHNICAL FIELD

The invention relates to compositions and methods for preparing membrane protein nanosheets. In particular, the methods employ an organic solvent for preparation of the nanosheets.

BACKGROUND

Biological membrane protein channels, synthetic channels, and carbon nanotubes have emerged as promising platforms for the development of separation membranes with precise molecular selectivity. Relative to state-of-the-art commercial membranes, biomimetic membranes incorporating these pore structures are expected to exhibit high permeability and selectivity because they possess a high density of channels with a well-defined pore geometry and functionality designed to exclude or pass specific components from complicated mixtures. Membrane protein-based biomimetic membranes studied thus far have been limited to small improvements in performance that are much lower than the orders of magnitude enhancement anticipated from early experiments. Current membrane protein-based biomimetic membranes show 2-3 times of an increase in permeability over commercial membranes with similar or worse selectivity. This has been attributed to the use of vesicular morphologies of channel-reconstituted liposomes and the low protein content in biomimetic matrices used for membrane fabrication. Unfortunately, these improved membrane technologies have not been capable of widespread application due to the use of non-scalable fabrication techniques used for membrane synthesis (e.g., detergent removal-based self-assembly techniques). Designing membranes with high packing densities of channel proteins with uniform pore sizes of ~0.5-1.5 nm with less material- and time-intensive synthesis techniques could provide a path to meet the ultimate promise of biomimetic membranes in this important solute size range.

Despite numerous attempts, successful integration of membrane proteins into practical membranes has remained a significant challenge. Existing methods for preparing membrane protein nanosheets and two-dimensional crystals are complex, time-consuming, and can be difficult. There has been an inability to use solvent-based methods due to incompatibility of solvents with proteins, which has limited the methods by which membrane protein nanosheets and two-dimensional crystals can be prepared. One existing method is a detergent removal method through dilution or dialysis. The detergent-based method typically takes multiple days to prepare nanosheets (e.g., 5 to 6 days). The specialized detergents used for such a process are expensive (~25 dollars/gram). An example of such a method is described in "High-Density Reconstitution of Functional Water Channels into Vesicular and Planar Block Copolymer Membranes," J. Am. Chem. Soc'y, by Kumar et al. Other methods previously employed, included magnetically directed crystallization. However, this type of method also takes multiple days and requires expensive equipment to perform. Thus, there is a need for methods of preparing nanosheets and two-dimensional crystals.

Accordingly, it is an objective of the invention to develop methods for preparing nanosheets and/or two-dimensional crystals comprising membrane proteins.

Another object of the invention is to provide nanosheets and/or two-dimensional crystals comprising membrane proteins.

A further object of the invention is to provide methods utilizing organic solvents for preparing nanosheets and/or two-dimensional crystals comprising membrane proteins.

Other objects, advantages and features of the present invention will become apparent from the following specification taken in conjunction with the accompanying drawings.

BRIEF SUMMARY OF PREFERRED EMBODIMENTS

A preferred embodiment includes novel methods of preparing membrane protein nanosheets or two-dimensional crystals using a solvent. The methods offer substantial improvements over existing methods for preparing membrane protein nanosheets and two-dimensional crystals, which can be complex, expensive, time-consuming, and difficult.

Preferably, the method comprises preparing a mixture of a polymer and a membrane protein solubilized in a solvent. The mixture is applied to a substrate and the solvent removed to form a dried nanosheet and/or two-dimensional crystal.

Preferably, the polymer comprises a block copolymer. In some embodiments, the block copolymer comprises one or more hydrophobic blocks of polybutadiene (PB) and one or more hydrophilic blocks of polyethylene oxide (PEO).

Preferably, the membrane protein comprises a pore or channel. Surprisingly the methods are effective for not only beta barrel membrane proteins but also the less stable alpha helical membrane proteins. In some embodiments, the membrane protein comprises one or more mutations to improve its thermal and/or solvent stability. In some embodiments, the membrane protein is a porin, a pore-forming toxin, or an aquaporin. In exemplary embodiments, the membrane protein is outer membrane protein F (OmpF), α-hemolysin (αHL), ferrichrome outer membrane transporter (FhuA), or aquaporin Z (AqpZ). In some embodiments, the mixture has a polymer to protein mass ratio of between about 10:1 and about 1:10.

Preferably, the mixture is applied to a substrate by spraying, pouring, extruding, squirting, or spreading. In some embodiments, the substrate comprises glass, plastic, composite, metal, or a mixture or combination thereof.

Preferably, the solvent comprises an organic solvent. In some embodiments, the organic solvent comprises chloroform, methanol, or the combination thereof. Preferably, the solvent is removed by evaporation. In some embodiments, the evaporation comprises air drying, heating, vacuum drying, or a combination thereof.

A preferred embodiment includes optionally rehydrating the dried nanosheet or two-dimensional crystal in a rehydration buffer. In some embodiments, the rehydration buffer comprises Tris, HEPES, MES, PBS, MOPS, or a mixture thereof.

A preferred embodiment includes nanosheets and two-dimensional crystals prepared by the methods and membranes comprising the nanosheets or two-dimensional crystals.

While multiple embodiments are disclosed, still other embodiments of the inventions will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE FIGURES

The following figures form part of the specification and are included to further demonstrate certain embodiments or various aspects of the invention. In some instances, embodiments of the invention can be best understood by referring to the accompanying figures in combination with the detailed description presented herein. The description and accompanying figures may highlight a certain specific example, a preferred embodiment, or a certain aspect of the invention. However, one skilled in the art will understand that portions of the example or aspect may be used in combination with other examples or aspects of the invention.

FIG. 1A shows the three distinct β-barrel channel proteins that were used: (i) OmpF from $E.\ coli$ (PDB: 2OMF) that excludes proteins but allows small sugars, nutrients and antibiotics to pass through, with in silico estimated pore sizes of 0.8×1.08 nm, (ii) FhuA ΔC/Δ4L from $E.\ coli$ that originally forms part of a larger pore complex for active ferrichrome-iron and antibiotic transports but is engineered with its central alpha-helical plug removed as a passive pore in this work, resultant pore size of 1.31×1.62 nm, (iii) alpha hemolysin, a self-assembled structure created by $Staphylococcus\ aureus$ to porate cell membranes, with an estimated pore size of 1.50×1.50 nm (PDB: 7AHL). FIG. 1B shows two self-assembly methods to construct high density 2D β-barrel channel protein-BCP crystals or nanosheets by self-assembly using (1) detergent dialysis method, a slow detergent removal process with a 6-day dialysis process, and (2) organic solvent extraction method, a 2-hour self-assembly process with addition of chloroform and methanol mixture to protein and polymers, then solvent evaporation, followed by aqueous rehydration. FIG. 1C is a schematic illustration of the layer-by-layer membrane fabrication procedure with densely packed β-barrel channel protein-BCP nanosheets on porous substrates. These scalable channel protein-incorporated biomimetic membranes achieved precise molecular selectivity while demonstrating high water permeability.

FIG. 7A shows the molecular weight cutoffs (MWCOs) measured were ~490 Da, ~480 Da, ~930 Da and ~1,130 Da for OmpF (solvent), OmpF (dialysis), αHL (dialysis), FhuA ΔC/Δ4L (dialysis) channel protein-embedded biomimetic membranes, respectively, as determined from filtration of dyes of various molecular weights and fitting to a sigmoidal model. FIG. 7B is a plot of water filtration volume vs time of OmpF, αHL, FhuA ΔC/Δ4L (dialysis) based biomimetic membranes (filtration under 5 psi), NP010 and GE commercial membranes (filtration under 50 psi). FIG. 7C shows the water permeability of three β-barrel channel protein-embedded biomimetic membranes were 293±51 LMH bar$^{-1}$, 724.5±225.9 LMH bar$^{-1}$, and 1,092±79.4 LMH bar$^{-1}$ for OmpF (dialysis), FhuA ΔC/Δ4L (dialysis), αHL (dialysis), demonstrating one or two order of magnitude higher permeability than commercial membranes.

FIG. 8A shows the molecular weight cutoff (MWCO) are 1091 Da for αHL (solvent) and 1133 Da for FhuA ΔC/Δ4L (solvent) nanosheet-based biomimetic membranes. FIG. 8B shows the water permeability of three β-barrel channel protein-embedded biomimetic membranes were 283±22 LMH bar$^{-1}$, 980.06 LMH bar$^{-1}$, and 1101.93 LMH bar$^{-1}$ for OmpF (solvent), FhuA ΔC/Δ4L (solvent), αHL (solvent), indicating performance similar to those by 2D nanosheets by dialysis method, which also show high water permeability and unique exclusion limits.

FIG. 10A is at a polymer to protein mass ratio of 1:3.3 and FIG. 10B is at a polymer to protein ratio of 1:2.5.

DETAILED DESCRIPTION

Figure 1A:
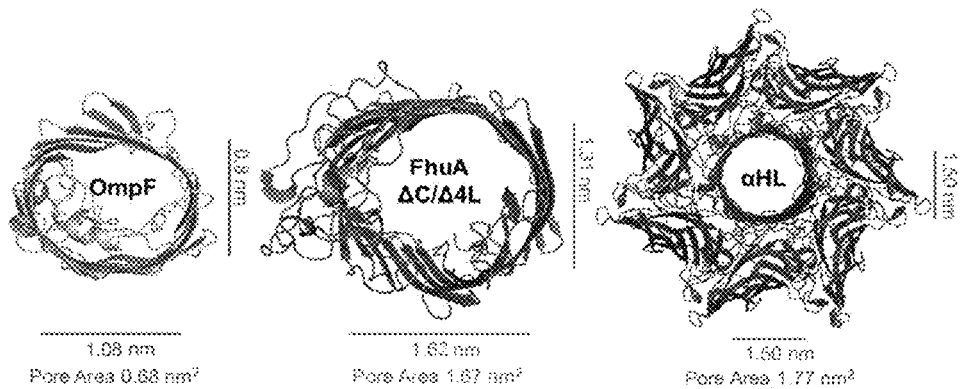
FIGS. 1A-C show stable β-barrel channel protein-polymer-based scalable membranes.

The present disclosure relates to nanosheets and two-dimensional crystals comprising membrane protein and methods of preparing the same with a solvent. The methods of preparing the membrane composition have many advantages over existing methods. For example, the nanosheets and two-dimensional crystals can be prepared faster than with existing methods. A further advantage of the present invention is that the methods provide a cost savings in terms of the methods themselves, equipment required, and chemicals required. Surprisingly, the methods can employ organic solvents in the preparation of the nanosheets and two-dimensional crystals. The embodiments of this invention are not limited to particular membranes or methods of using membranes, which can vary greatly without departing from the scope of the invention.

Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

It is to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

The term "about," as used herein, refers to variation in the numerical quantity that can occur, for example, through typical measuring techniques and equipment, with respect to any quantifiable variable, including, but not limited to, mass, volume, time, temperature, distance, molecular weight, and water permeability. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations. The term "about" also encompasses amounts that differ due to different equilibrium conditions for a composition resulting from a particular initial mixture. Whether or not modified by the term "about," the claims include equivalents to the quantities.

As used herein, the term "analog" means a molecular derivative of a molecule. The term is synonymous with the terms "structural analog" or "chemical analog."

The methods and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

As used herein, the prefix "oligo-" refers to a molecular complex comprised of between two and ten monomeric units. For example, oligosaccharides are comprised of between two and ten monosaccharides. Furthermore, unless otherwise specifically limited, the term "oligo-" shall include all possible isomeric configurations of the molecule, including, but are not limited to isotactic, syndiotactic and random symmetries, and combinations thereof. Furthermore, unless otherwise specifically limited, the term "oligo-" shall include all possible geometrical configurations of the molecule.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The terms "water soluble" and "water miscible" as used herein, means that the component is soluble or miscible in water at 25° C. preferably at a concentration of 0.01 wt. %, more preferably at 0.1 wt. %, and most preferably at 1 wt. %.

Nanosheets, Two-Dimensional Crystals and Methods of Preparing the Same

The present disclosure relates to nanosheets and two-dimensional crystals comprised of a membrane protein. In a preferred embodiment of the invention, the nanosheets and two-dimensional crystals are used in a membrane. The nanosheets, two-dimensional crystals, and membranes comprised of the same are particularly suitable for precision separations. Thus, the membrane compositions can be used in a variety of separations, biomimetic devices, sensors, drug delivery devices, etc. Precision separations can be performed with the use of the membrane compositions in filtration devices, including, but not limited to, masks, air purifiers, water filters, desalination devices, and biomimetic devices. The compositions described herein can provide substantial energy savings in applications ranging from water treatment to small molecule bioseparations.

The nanosheets and two-dimensional crystals can be prepared by dissolving a polymer in solvent, dissolving a protein in solvent, and combining the two to form a combined solution. In a preferred embodiment, the polymer is dissolved in solvent, then the protein is added and dissolved in the solution with the polymer to form a combined solution. In an alternative embodiment, the protein is dissolved in solvent, then the polymer is dissolved in the solution with the protein to form a combined solution. In a further embodiment, the polymer and protein are dissolved separately in solvent and then combined to form a combined solution. In still a further embodiment, the protein and polymer are dissolved together in solvent to form a combined solution.

Preferably, the polymer and membrane protein are in a mass ratio of between about 10:1 and about 1:10, between about 9:1 and about 1:9, between about 8:1 and about 1:8, between about 7:1 and about 1:7, between about 6:1 and about 1:6, between about 5:1 and about 1:5, between about 4:1 and about 1:4, between about 3:1 and about 1:3, between about 2:1 and about 1:2, at about 1:1. In some embodiments, the mass ratio of the polymer to membrane protein is between about 1:10 and about 1:2.

In a preferred embodiment the combined solution is mixed. Preferably, the combined solution is mixed homogeneously. Any suitable method of mixing can be performed. Preferred methods of mixing include, but are not limited to, sonicating, manual mixing, automatic mixing, stirring, or a combination thereof.

The combined solution is applied to a substrate. The substrate can be of any suitable size for preparation of the desired membrane size. In a preferred embodiment, the substrate is suitable for preparation of a membrane. Preferably the substrates can comprise glass, plastic, composite, metal, or a mixture or combination thereof. The combined solution can be applied to a substrate by any suitable method, including, but not limited to, spraying, pouring, extruding, squirting, or otherwise applying. Optionally, the combined solution can be spread on the substrate.

Once applied to the substrate, the solvent is evaporated from the combined solution. Any suitable means of evaporating can be applied. Preferred evaporation techniques include, but are not limited to, air drying, heating, vacuum drying, or a combination thereof. If using heat as an evaporation technique, it is preferably applied at a temperature of less than the melting point of the polymer. A preferred method of evaporation is heating and vacuum drying.

Once dried, a nanosheet and/or two-dimensional crystal comprising a polymer and a membrane protein can be removed from the substrate. Optionally, a buffer can be added to the dried nanosheet and/or two-dimensional crystal. In an embodiment, the nanosheet and/or two-dimensional crystal can be used to prepare a membrane on the substrate; in which case the membrane can be removed from the substrate. The nanosheet and/or two-dimensional crystal comprising a polymer and a membrane protein can be incorporated into a membrane. The membrane can be incorporated into a separation device.

Membrane Proteins

The methods and compositions comprise a membrane protein. One or more types of membrane proteins may be used depending on the effect that is desired in the final membrane. Preferably the membrane protein comprises a pore or a channel. Membrane proteins suitable for inclusion in the membranes are for instance selected from, but not limited to, membrane proteins found in The Transporter Classification Database (TCDB; www.tcdb.org). The TCDB is an International Union of Biochemistry and Molecular Biology (IUBMB)-approved classification system for membrane transport proteins. For example, suitable native, recombinant, and engineered membrane proteins may include but are not limited to ABC transporters, ATPases, G-protein coupled receptors, holins, ion channels, major intrinsic proteins (including aquaporin water channels), mechanosensitive channels, outer membrane pore-forming proteins (porins), pore-forming toxins, rhodopsins, and the like. Additional pores or channels may include mutated or engineered pores or channels with increased thermal or solvent stability, and performance properties such as "always open" pores or channels. The embodiments of this invention are not limited to particular membrane protein, which can vary and are understood by skilled artisans.

In some embodiments, the membrane protein is a beta barrel membrane protein or an alpha helical membrane protein. Although known to be less stable than beta barrel membrane proteins, alpha helical membrane proteins also maintain their structure when exposed to solvents during the short processing time utilized. In some embodiments, the membrane protein is a porin, a pore-forming toxin, or an aquaporin.

Porins are beta barrel membrane proteins present in the outer membrane of gram-negative bacteria and some gram-positive Mycobacteria, the outer membrane of mitochondria, and the outer chloroplast membrane. In an exemplary embodiment, the porin is outer membrane protein F (OmpF) from $E.$ $coli$. In another exemplary embodiment, the porin is FhuA from $E.$ $coli$ that originally forms part of a larger pore complex for active ferrichrome-iron and antibiotic transports. FhuA ΔC/Δ4L is engineered with its central alpha-helical plug removed to function as a passive pore. All known porins are useful in the invention.

Pore-forming toxins (also known as pore-forming proteins) are produced by bacteria as well as other organisms including earthworms, which produce the pore-forming toxin lysenin. Pore-forming toxins may be beta barrel pore-forming toxins (including α-hemolysin, Panton-Valentine leucocidin, Clostridial Epsilon-toxin) or alpha helical pore-forming toxins (including haemolysin E, actinoporins, Corynebacterial porin B). In an exemplary embodiment, the pore-forming toxin is α-hemolysin (αHL), a self-assembled structure created by *Staphylococcus aureus* to porate cell membranes.

Aquaporins (AQPs) are integral membrane proteins from a larger family of major intrinsic proteins (MIPs) that form pores in the membrane of biological cells, mainly facilitating transport of water between cells. Aquaporin proteins are composed of a bundle of six transmembrane α-helices. All known aquaporin water channels (including but not limited to AQP0, AQP1, AqpZ, AQP4, SoPIP2; 1, NtAQP1, AQP9, AqpX) are useful in the invention. In an exemplary embodiment, the aquaporin is AqpZ from *Rhodobacter sphaeroides*.

Preferably, the membrane protein comprises between about 10 wt. % and about 90 wt. % of the nanosheet or two-dimensional crystal, more preferably between about 15 wt. % and about 85 wt. % of the nanosheet or two-dimensional crystal, most preferably between about 20 wt. % and about 80 wt. % of the nanosheet or two-dimensional crystal.

Preferably, the membrane protein comprises between about 0.1 wt. % and about 60 wt. % of the combined solution, more preferably between about 0.5 wt. % and about 55 wt. % of the combined solution, most preferably between about 1 wt. % and about 50 wt. % of the combined solution.

Polymer

The methods and compositions comprise a polymer. Preferred polymers include, but are not limited to, a thermoplastic, a thermoset, or a combination thereof. Preferably, the polymer is a block copolymer.

Various types of amphiphilic copolymers can be used. In one embodiment, the copolymer is an ABA copolymer, where A is hydrophilic and B is hydrophobic where A is the same or different hydrophilic segments and B is a hydrophobic B segment. Thus, the term "ABA copolymer" includes an ABC copolymer, where the hydrophilic segments A and C are different.

The block copolymer includes at least one segment B that includes a hydrophobic polymer. Any of a number of hydrophobic polymers can be used, such as, but not limited to, polysiloxane such as polydimethylsiloxane and polydiphenylsiloxane, perfluoropolyether, polystyrene, polyoxypropylene, polyvinylacetate, polyoxybutylene, polyisoprene, polybutadiene, polyvinylchloride, polyalkylacrylate (PAA), polyalkylmethacrylate, polyacrylonitrile, polypropylene, PTHF, polymethacrylates, polyacrylates, polysulfones, polyvinylethers, and poly(propylene oxide), and copolymers thereof.

In some embodiments, the hydrophobic segment contains a predominant amount of hydrophobic monomers. A hydrophobic monomer is a monomer that typically gives a homopolymer that is insoluble in water and can absorb less than 10% by weight of water.

Suitable hydrophobic monomers are C1-C18 alkyl and C3-C18 cycloalkyl acrylates and methacrylates, C3-C18 alkylacrylamides and -methacrylamides, acrylonitrile, methacrylonitrile, vinyl C1-C18 alkanoates, C2-C18 alkenes, C2-C18 haloalkenes, styrene, (lower alkyl)styrene, C4-C12 alkyl vinyl ethers, C2-C10 perfluoro-alkyl acrylates and methacrylates and correspondingly partially fluorinated acrylates and methacrylates, C3 through C12 perfluoroalkylethylthiocarbonylaminoethyl acrylates and methacrylates, acryloxy- and methacryloxyalkylsiloxanes, N-vinylcarbazole, C1 through C12 alkyl esters of maleic acid, fumaric acid, itaconic acid, mesaconic acid, vinyl acetate, vinyl propionate, vinyl butyrate, vinyl valerate, chloroprene, vinyl chloride, vinylidene chloride, vinyltoluene, vinyl ethyl ether, perfluorohexyl ethylthiocarbonylaminoethyl methacrylate, isobornyl methacrylate, trifluoroethyl methacrylate, hexafluoroisopropyl methacrylate, hexafluorobutyl methacrylate, tristrimethylsilyloxysilylpropyl methacrylate (TRIS), and 3-methacryloxypropylpentamethyldisiloxane.

In some embodiments, the hydrophobic polymer is one which displays a relatively high oxygen diffusion rate there through, such as, but not limited to, polysiloxanes, perfluoroalkyl ethers, specific unsaturated polymers, and polysulfones. In one embodiment, the hydrophobic polymer is a polysiloxane block having terminal alkylene groups.

In some embodiments, the hydrophobic polymer includes a perfluoroalkyl-polyether block. In other embodiments, the hydrophobic polymer includes an unsaturated polymer, such as a polymer of a conjugated aliphatic or alicyclic diene, which may be substituted by halogen or lower alkyl, a polymer of an alkyne or dialkyne, which may be substituted by lower alkyl or trimethylsilyl, a copolymer of a conjugated diene and a hydrophilic or hydrophobic vinylic monomer, and also partially hydrated derivatives of these compounds.

Specific examples of polymers of conjugated dienes are cis-, trans-, iso- or syndiotactic poly-1,2-butadiene, poly-1,4-butadiene or polyisoprene, poly-pentenamer, polychloroprene and polypiperylen. Other examples of copolymers are butadiene- or isoprene-copolymers with hydrophilic or hydrophobic vinylic monomers, such as acrylonitrile, styrene, acrylic acid or hydroxyethylmethacrylate. An example of a polyalkyne is poly-1-trimethylsilyl-propyne. In some embodiments, examples of polymers included unsaturated polymers are syndiotactic poly-1,2-butadiene, poly-1,4-butadiene and polyisoprene. An especially preferred unsaturated polymer is poly-1-trimethylsilyl-propyne. Another especially preferred unsaturated polymer is poly-1,4-butadiene. The hydrophobic polymer may include a single type of polymer or more than one type of polymer, such as two or more of those discussed above. The mean molecular weight of one segment B is in the range from about 500 to about 50,000, preferably in the range from about 800 to about 15,000, more preferably in the range of about 1,000 to 12,000, particularly preferably in the range from about 5,000 to about 12,000.

In some embodiments in addition to the hydrophobic segment B, the amphiphilic segmented copolymer includes at least one segment A which includes at least one hydrophilic polymer, such as, but not limited to, polyoxazoline, polyethylene glycol, polyethylene oxide, polyvinyl alcohol, polyvinylpyrrolidone, polyacrylamide, poly(meth)acrylic acid, polyethylene oxide-co-polypropyleneoxide block copolymers, poly(vinylether), poly(N,N-dimethylacrylamide), polyacrylic acid, polyacyl alkylene imine, polyhydroxyalkylacrylates such as hydroxyethyl methacrylate (HEMA), hydroxyethyl acrylate, and hydroxypropyl acrylate, polyols, and copolymeric mixtures of two or more of the above mentioned polymers, natural polymers such as polysaccharides and polypeptides, and copolymers thereof, and polyionic molecules such as polyallylammonium, polyethyleneimine, polyvinylbenzyltrimethylammonium, polyaniline, sulfonated polyaniline, polypyrrole, and polypyridinium, polythiophene-acetic acids, polystyrenesulfonic acids, zwitterionic molecules, and salts and copolymers thereof.

In some embodiments, the hydrophilic segment preferably contains a predominant amount of hydrophilic monomers. A hydrophilic comonomer is a monomer that typically gives a homopolymer that is soluble in water or can absorb at least 10% by weight of water.

Suitable hydrophilic monomers are hydroxyl-substituted lower alkyl acrylates and methacrylates, acrylamide, methacrylamide, (lower alkyl) acrylamides and methacrylamides, N,N-dialkyl-acrylamides, ethoxylated acrylates and methacrylates, polyethyleneglycol-mono methacrylates and polyethyleneglycolmonomethylether methacrylates, hydroxyl-substituted (lower alkyl)acrylamides and methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino(lower alkyl)-(where the term amino also includes quaternary ammonium), mono(lower alkylamino)(lower alkyl) and di(lower alkylamino)(lower alkyl) acrylates and methacrylates, allyl alcohol, 3-trimethylammonium 2-hydroxypropylmethacrylate chloride (Blemer.QA, for example from Nippon Oil), dimethylaminoethyl methacrylate (DMAEMA), dimethylaminoethylmethacrylamide, glycerol methacrylate, and N-(1,1-dimethyl-3-oxobutyl)acrylamide.

In some embodiments, the segment A includes a polymer displaying a relatively high water or ion diffusion rate there through. Specific examples of hydrophilic monomers from which such polymers can be made are cyclic imino ethers, vinyl ethers, cyclic ethers including epoxides, cyclic unsaturated ethers, N-substituted aziridines, beta-lactones and beta-lactams. Further suitable monomers include ketene acetals, vinyl acetals and phosphoranes. Suitable cyclic imino ethers include 2-oxazoline. If a 2-oxazoline having an alkenyl group in 2 position is used as hydrophilic monomer, a polymerizable unsaturated group is provided within segment A (in a side chain) of the amphiphilic segmented copolymer to serve as the polymerizable unsaturated group necessary for the final polymerization to obtain a polymeric product or as an additional polymerizable unsaturated group which offers the possibility of direct crosslinking in the preparation of the polymer. In some embodiments, the cyclic imino ether is 2-methyloxazoline. The most preferred vinyl ethers are methyl vinyl ether, ethyl vinyl ether and methoxy ethyl vinyl ether.

In some embodiments, the mean molecular weight of one segment A is in the range from about 500 to about 50,000, from about 800 to about 15,000, from about 1,000 to 12,000, particularly from about 5,000 to about 12,000.

Preferred block copolymers, include, but are not limited to, an amphiphilic diblock or triblock block copolymer comprising one or more hydrophobic blocks selected from the group consisting of polybutadiene (PB), polydimethylsiloxane (PDMS), polypropylene (PP), polypropylene oxide (PPO), polyethylethylene (PEE), polyisobutylene (PM), polyisoprene (PI), polycaprolactone (PCL), polystyrene (PS), fluorinated polymers, and polymethylmethacrylate (PMMA); and one or more hydrophilic blocks selected from the group consisting of polymethyloxazoline (PMOXA), polyethyloxazoline (PEtOXA), and polyethylene oxide (PEO). In particular embodiments of methods herein, the block copolymer comprises one or more hydrophobic blocks of polybutadiene (PB) and one or more hydrophilic blocks of polyethylene oxide (PEO).

Preferably, the polymer comprises between about 10 wt. % and about 90 wt. % of the nanosheet or two-dimensional crystal, more preferably between about 15 wt. % and about 85 wt. % of the nanosheet or two-dimensional crystal, most preferably between about 20 wt. % and about 80 wt. % of the nanosheet or two-dimensional crystal.

Preferably, the polymer comprises between about 0.1 wt. % and about 60 wt. % of the combined solution, more preferably between about 0.5 wt. % and about 55 wt. % of the combined solution, most preferably between about 1 wt. % and about 50 wt. % of the combined solution.

Preferably, the polymer comprises between about 0.01 wt. % and about 20 wt. % of the combined solution, more preferably between about 0.1 wt. % and about 15 wt. % of the combined solution, most preferably between about 0.5 wt. % and about 10 wt. % of the combined solution.

Solvent

The methods employ a solvent. Preferably, the solvent is an organic solvent. Preferred solvents include nonpolar solvents, polar protic solvents, and mixtures thereof. In some embodiments, the solvent is a water miscible solvent. Preferred solvents have a boiling point of less than 80° C., less than 75° C., or less than 70° C. Preferred solvents include, but are not limited to, chloroform, decane, dodecane, heptane, hexane, methanol, or a mixture thereof. The solvent used herein can be of a single solvent or a mixture of many different solvents.

Preferably, the solvent comprises between about 0.1 wt. % and about 99 wt. % of the combined solution, more preferably between about 0.5 wt. % and about 95 wt. % of the combined solution, most preferably between about 1 wt. % and about 90 wt. % of the combined solution.

Buffer

The methods can optionally employ a buffer. Preferably the buffer is an aqueous buffer. Preferred buffers include, but are not limited to, Tris (tris(hydroxymethyl)aminomethane), HEPES (N-[2-hydroxyethyl]piperazine-N'-(2-ethanesulphonic) acid), MES (2-(N-morpholino)ethanesulfonic acid), PBS (phosphate buffered saline), MOPS (3-[N-morpholino]propanesulphonic acid), or a mixture thereof. Additional buffers suitable for use in the disclosed methods include Bis-tris (2-bis[2-hydroxyethyl]amino-2-hydroxymethyl-1,3-propanediol), ADA (N-[2-acetamido]-2-iminodiacetic acid), ACES (2-[2-acetamino]-2-aminoethanesulphonic acid), PIPES (1,4-piperazinediethanesulphonic acid), MOPSO (3-[N-morpholino]-2-hydroxypropanesulphonic acid), Bis-tris propane (1,3 bis[tris(hydroxymethyl)methylaminopropane]), BES (N,N-bis[2-hydroxyethyl]-2-aminoethanesulphonic acid), TES (2-[2-hydroxy-1,1-bis(hydroxymethyl)ethylamino]ethanesulphonic acid), DIPSO (3-N,N-bis[2-hydroxyethyl]amino-2-hydroxypropanesulphonic) acid), MOBS (4-N-morpholinobutanesulphonic acid), TAPSO (3 [N-tris-hydroxymethyl-methylamino]-2-hydroxypropanesulphonic acid), Tris (2-amino-2-[hydroxymethyl]-1,3-propanediol), HEPPSO (N-[2-hydroxyethyl]piperazine-N'-[2-hydroxypropanesulphonic]acid), POPSO (piperazine-N,N'-bis[2-hydroxypropanesulphonic]acid), TEA (triethanolamine), EPPS (N-[2-hydroxyethyl]-piperazine-N'-[3-propanesulphonic]acid), Tricine (N-tris[hydroxymethyl]methylglycine), Glycylglycine (diglycine), Bicine (N,N-Bis(2-hydroxyethyl)glycine), HEPBS (N-[2-hydroxyethyl]piperazine-N'-[4-butanesulphonic]acid), TAPS (N-tris[hydroxymethyl]methyl-3-aminopropanesulphonic]acid), AMPD (2-amino-2-methyl-1,3-propanediol), TABS (N-tris[hydroxymethyl]methyl-4-aminobutanesulphonic acid), AMPSO (3-[(1,1-dimethyl-2-hydroxyethyl)amino]-2-hydroxypropanesulphonic acid), CHES (2-(N-cyclohexylamino)ethanesulphonic acid), CAPSO (3-[cyclohexylamino]-2-hydroxy-1-propanesulphonic acid), AMP (2-amino-2-methyl-1-propanol), CAPS (3-cyclohexylamino-1-propanesulphonic acid), or CABS (4-[cyclohexylamino]-1-butanesulphonic acid).

Preferably, the buffer comprises between about 0.01 wt. % and about 20 wt. % of the nanosheet or two-dimensional crystal, more preferably between about 0.1 wt. % and about 15 wt. % of the nanosheet or two-dimensional crystal, most preferably between about 0.5 wt. % and about 10 wt. % of the nanosheet or two-dimensional crystal.

Substrate

Any suitable substrate can be used. Preferably the substrates can comprise glass, plastic, composite, metal, or a mixture or combination thereof. Preferred substrates are suitable for preparing membranes. In an exemplary embodiment, the solvent is evaporated on a glass surface.

It is understood that modifications which do not substantially affect the activity the various embodiments of this invention are also provided within the definition of the invention provided herein. Accordingly, the following examples are intended to illustrate but not limit the present invention.

EXAMPLES

Figure 1B:
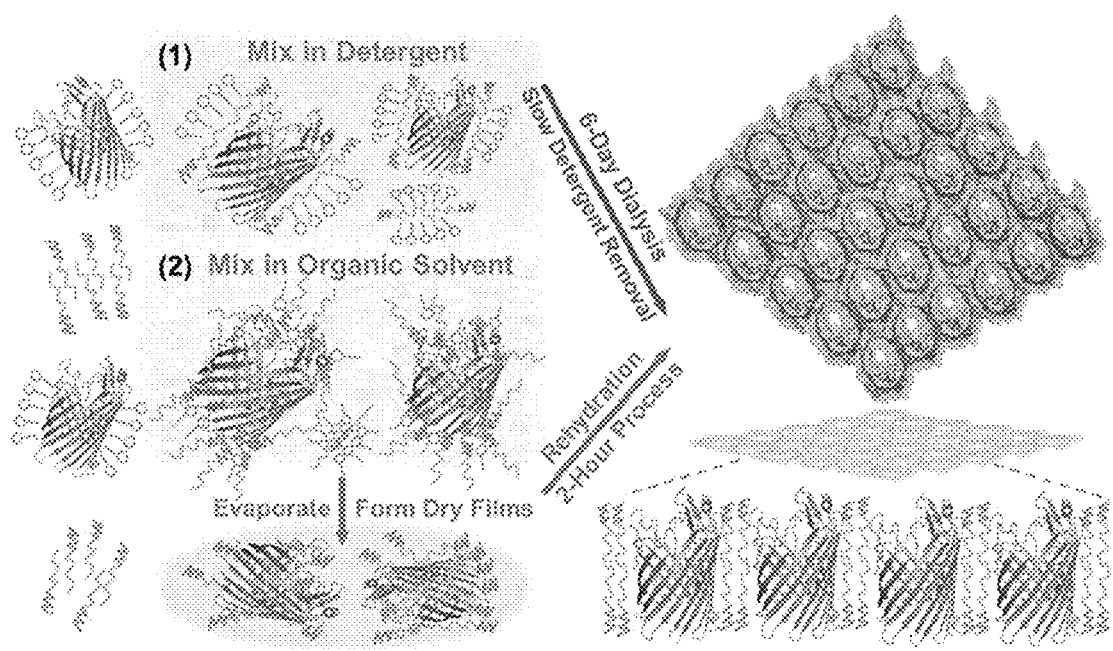

Example 1: Rapid Fabrication of Precise, High-Throughput Filters from Membrane Protein Nanosheets We present a comprehensive approach to construct biomimetic membranes beginning with the scalable synthesis of two-dimensional (2D) crystals and nanosheets that contain a high packing density of β-barrel proteins. (FIG. 1). The membranes fabricated from these 2D materials showed significant improvements in membrane productivity (water permeability) and maintained designed selectivity as a result of the high porosities and unitary pore shapes of the protein channels. Three different pore-forming β-barrel channel proteins, outer membrane protein F (OmpF), a mutated version of a bacterial ferrichrome outer membrane transporter (designated FhuA ΔC/Δ4L), and a channel forming protein toxin from *Staphylococcus aureus*, alpha-hemolysin (αHL), were selected to demonstrate this approach. These proteins possess unique elliptical pore dimensions of 0.8×1.08 nm, 1.31×1.62 nm, and 1.50×1.50 nm for OmpF, FhuA ΔC/Δ4L, and αHL, respectively (FIG. 1A). Simultaneously achieving precise control over pore sizes in this range, while maintaining uniformity in pore size and achieving a high porosity, is quite difficult using current membranes. Membrane protein 2D crystal arrays or nanosheets were created by reconstituting these channel proteins into poly(butadiene)-b-poly(ethylene oxide) (PB-PEO) di-block copolymers (BCPs) through two self-assembly strategies: detergent removal by dialysis (dialysis method) and self-assembly from BCP-membrane protein films deposited using organic solvent evaporation (solvent method) (FIG. 1B). The dialysis method is known to be capable of assembling protein and artificial water channels into ordered 2D crystal arrays and artificial channels into highly packed 2D nanosheets. However, this "slow dialysis" method takes ~6 days to complete and translating such a time-intensive process to larger scales is not practical. In this work, we introduce a unique solvent-based method for the preparation of 2D protein channel nanosheets. The surprising success in formation of nanosheets and 2D crystals of channel proteins with BCPs by the solvent method resulted in a significant decrease in the process time from 6 days to ~2 hours. Moreover, it had the added benefit of reducing the usage of membrane protein-compatible detergent, which is often a high-cost specialty chemical.

Reconstitution of β-Barrel Protein Channels into Porous 2D Nanosheets 2D materials with uniformly-sized internal pores have various advantages in terms of membrane development. Porous sheet-like structures can be used to form defect-free but thin selective layers that lead to high productivity. Unitary pore structures can provide desirable molecular selectivity properties based primarily on molecular sieving effects.

Figure 2:
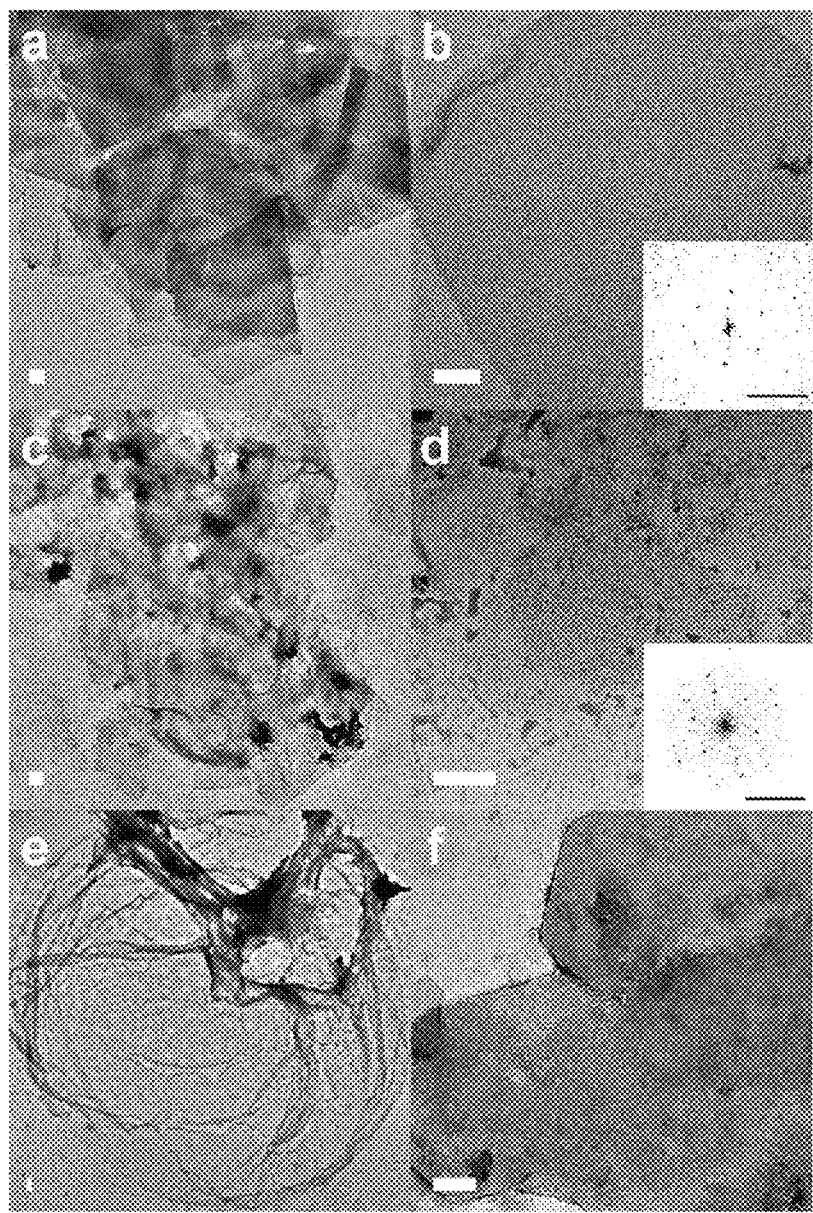
FIG. 2 shows 2D crystals or nanosheets of three β-barrel channel proteins reconstituted in BCP membrane matrices. Negative-stain transmission electron microscopy (TEM) images of OmpF 2D crystals prepared by dialysis (panel a) and solvent method (panel c) illustrates the characteristic morphologies of microscale 2D flat nanosheets. TEM images at high magnification with diffraction spots (insets) by fast Fourier transformation (FFT) of OmpF crystal images formed by dialysis (panel b) and solvent method (panel d) reveal the high degree of protein incorporation and crystalline structures. Negative-stain TEM images of αHL nanosheets (panel e) and FhuA ΔC/Δ4L (panel f) constructed by a dialysis method demonstrate 2D nanosheet formation. The scale bar is 100 nm and the scale bar in the insets is 10 nm$^{-1}$.

Three pore-forming β-barrel membrane proteins, OmpF, FhuA ΔC/Δ4L, and αHL, were selected based on their unique pore dimensions of 0.8×1.08 nm, 1.31×1.62 nm, and 1.50×1.50 nm, respectively, and reconstituted into 2D porous nanosheet structures. Amphiphilic PB-PEO BCPs were used as membrane matrices due to their higher chemical and mechanical stability compared to native lipids as well as their physical and chemical compatibility for membrane protein insertion. We first used a dialysis-based method for the formation of 2D nanosheet structures. In this method, the assembly kinetics of the proteins and BCPs are controlled through the gradual removal of high concentrations of detergents from a ternary mixture of protein, BCP, and detergent via dialysis (FIG. 1B). Assembly of OmpF proteins and PB-PEO BCPs using this method resulted in hexagonally-packed 2D protein crystals at polymer to protein ratios (PoPR, w/w) of 0.2-0.6. As observed by negative-stain transmission electron microscopy (TEM), micron-scale BCP-OmpF crystals were formed using the dialysis methods (FIG. 2). Fast Fourier transform (FFT) analysis of the electron diffraction pattern from TEM with the Focus software (FIG. 2) identified a hexagonal unit cell with lattice dimensions of a=b=~18 nm and γ=120. These dimensions indicate a pore packing density of ~$3.2×10^4$ pores $\mu m^{-2}$. This pore density represents the ultimate packing density of OmpF in block copolymers and demonstrates that the protocols we use for membrane proteins leads to a high-performance material and provides a way to get over the limited packing density of ~$10^3$ pores $\mu m^{-2}$ in vesicle-based systems. A similar dialysis protocol was also applied to FhuA ΔC/Δ4L and αHL proteins with PoPR of 0.2-0.35 and 0.25-0.4, respectively, in order to prepare highly packed membrane protein-BCP 2D nanosheets. Both FhuA ΔC/Δ4L and αHL proteins were successfully integrated into 2D nanosheet structures (FIG. 2). No evidence of crystallinity was seen for these two proteins.

Removing detergents via dialysis is a well-established, but slow method of preparing membrane protein 2D crystals and nanosheets in lipids and more recently in polymers. Generally, this process takes 3-6 days to be completed. Furthermore, membrane protein-BCP 2D crystal formation by dialysis requires a large amount of specialty non-ionic detergent per preparation, which could be a factor limiting the scalability of this technique. Hence, to shorten the time required for 2D nanosheet assembly and minimize the usage of detergents, we explored a new approach to prepare 2D protein crystals and nanosheets, which is referred to as the solvent method in this work. This new approach was inspired by reports on the extraction of hydrophobic membrane proteins from native cell membranes using organic solvents. The high stability of the β-barrel structure also provided an impetus to pursue the development of this technique, which relies on the hypothesis that the β-barrel proteins used would maintain their structure when exposed to solvents during the short processing time utilized. While not needed in this effort, a different β-barrel protein was mutated to improve its thermal and solvent stability indicating that the solvent resistance of these proteins can be even further evolved, if needed, in future implementations.

The solvent method utilized included three steps: (1) mixing proteins and BCPs in a methanol/chloroform (MeOH/CHCl$_3$) mixture (50% v/v) at specific PoPRs, (2) evaporating solvents to form protein/BCP films on glass surfaces, and (3) rehydrating the protein-BCP films using aqueous buffer solutions (FIG. 1B). The hydrophobic outer surfaces of the selected membrane proteins allowed them to be readily dissolved in the MeOH/CHCl$_3$ solvent mixture. We propose that, upon addition of BCPs dissolved in organic solvents to the protein solution, the hydrophilic surfaces of the β-barrel proteins were associated with hydrophilic PEO blocks and protected from the organic solvent environment by the hydrophobic PB block. This is similar to the protein stabilizing mechanism demonstrated in a recent study on protecting protein structure and function in organic solvents through the use of heteropolymers containing random hydrophobic and hydrophilic blocks of predefined domain sizes. During the solvent evaporation step, the polymer/BCP are mixed with detergent containing membrane proteins to form films containing detergent, BCP and membrane proteins. Subsequent film rehydration enables detergents to be diluted below their critical micelle concentration (cmc), allowing them to escape from protein/BCP/detergent complexes to the aqueous buffer solution. This detergent removal likely induces membrane protein-BCP re-orientation into assembled 2D structures. The solvent method required just ~2 hours with much lower detergent use and is thus more time and resource efficient.

For the dialysis method, purified membrane proteins were mixed with PB-PEO micelles in 65 μL rehydration buffer (20 mM Hepes, 10 mM MgCl$_2$, 100 mM NaCl and 3 mM NaN$_3$, pH7.4) containing 4% (w/v) OG at PoPr (ranging from 0.17 to 0.6), with final protein concentration at 1 mg mL$^{-1}$. The membrane protein/BCP mixture was transferred into 60 μL dialysis buttons covered with a 12-14 kDa cut-off dialysis membrane. Detergents were slowly removed by doubling the crystallization buffer volume with detergent-free rehydration buffer twice a day. When the final OG concentration reached 0.25% (w/v), the crystallization buffer was replaced by detergent-free rehydration buffer three times to further remove the detergent.

For the solvent method, 130 μg purified membrane proteins and BCPs were mixed to a 5 mL MeOH/CHCl$_3$ solvent mixture (50 mL, v/v) at different polymer to protein mass ratio (PoPr) (0.17-0.4). The solvent in the ternary mixture of protein/BCP/detergent was removed by rotary evaporation with 120 rpm for 1-2 h and optionally put into high vacuum chamber overnight to completely remove organic solvent. The resulting membrane protein/BCP dry films were rehydrated in 400 μL rehydration buffer to assemble membrane protein-BCP nanosheets and crystals.

Figure 3:
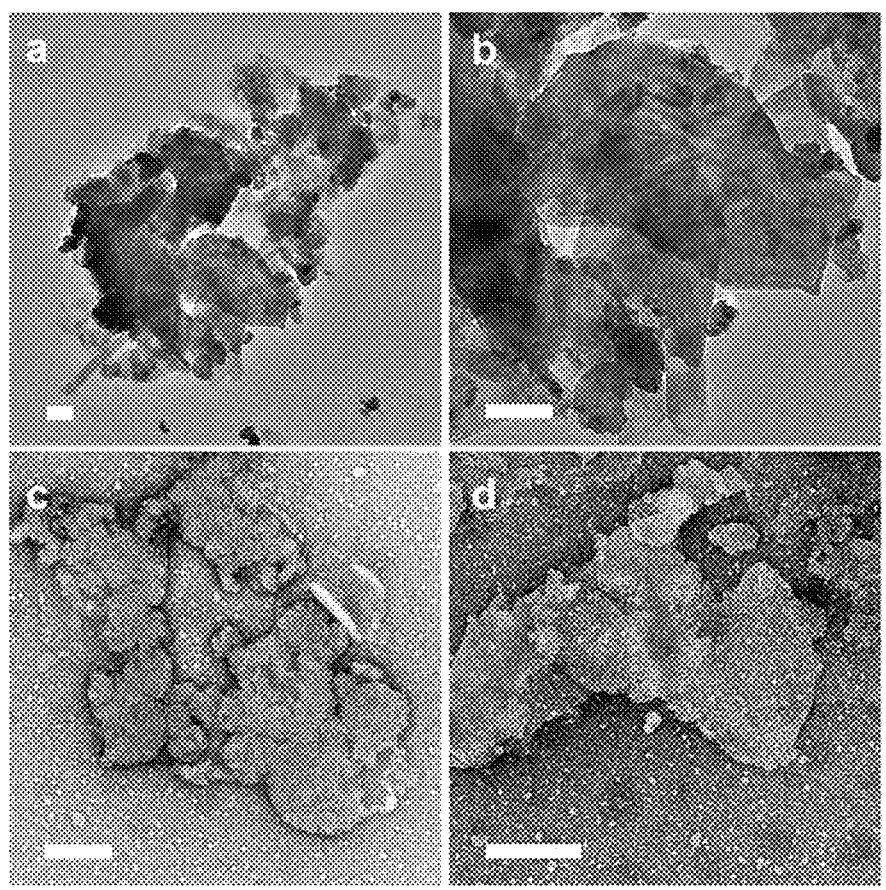
FIG. 3 shows 2D crystals or nanosheets of αHL and FhuA ΔC/Δ4L reconstituted in BCPs by the solvent method. Negative-stain transmission electron microscopy (TEM) images of FhuA ΔC/Δ4L (panel a and b) and αHL nanosheets (panel c and d). The scale bar is 200 nm.

The success of using the solvent method in the preparation of porous protein nanosheets was confirmed by TEM analysis. OmpF-BCP nanosheets prepared using the solvent method showed identical crystal forms to the OmpF crystals (hexagonal unit cells as inferred from the FFT patterns) prepared using the dialysis method (FIG. 2). Successful formation of nanosheets of αHL and FhuA ΔC/Δ4L proteins was also identified by TEM analysis as shown in FIG. 2 and FIG. 3.

Figure 4:
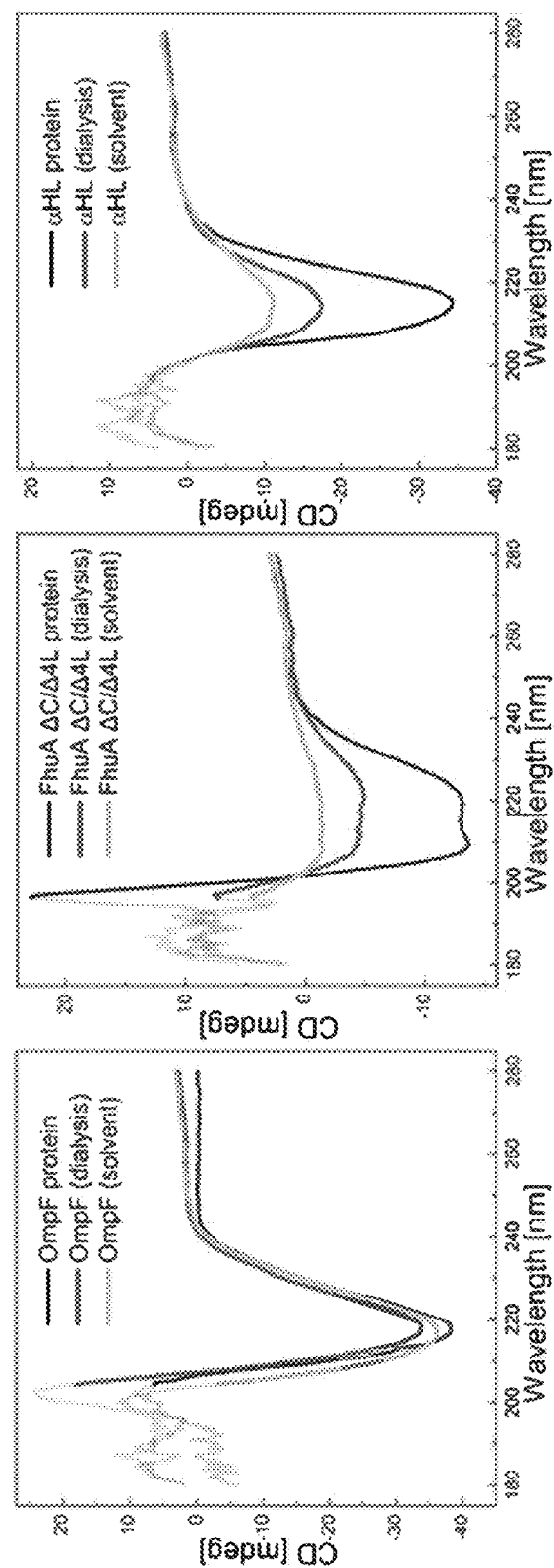
FIG. 4 shows that the β-barrel structures of OmpF, FhuA ΔC/Δ4L and αHL were preserved after the solvent based crystallization process. Circular dichroism spectroscopy (CD) results of β-barrel channel protein and protein-copolymer crystals or nanosheets using a dialysis and solvent method are shown. All quantitative analyses were fitted by multivariate secondary structure analysis from JASCO software (JWMVS-529 Multivariate SSE analysis, JASCO). Generally, the peak positions less than 200 nm could not be characterized due to the strong absorption of rehydration buffer at short wavelengths. The lower peaks from crystals resulted from low protein concentrations in crystal solutions and adsorption flattening optical effects but the essential features are preserved between the two self-assembly methods as described in the text.
Figure 5:
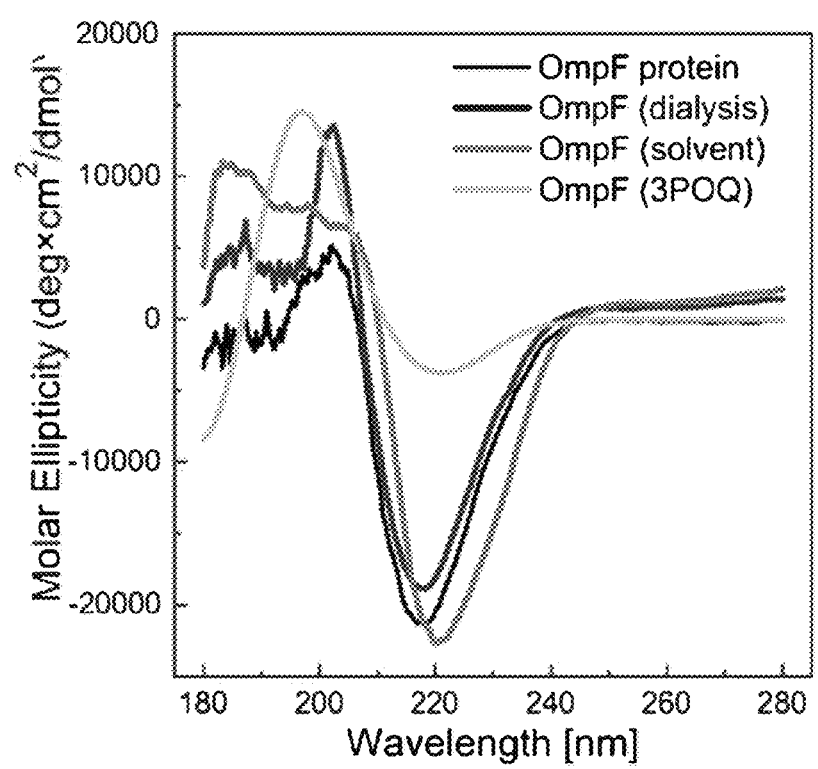
FIG. 5 shows a comparison of CD spectra of OmpF, OmpF crystal (dialysis), OmpF crystal (solvent), and OmpF in lipid cubic phases (PDB: 3POQ).
Figure 6:
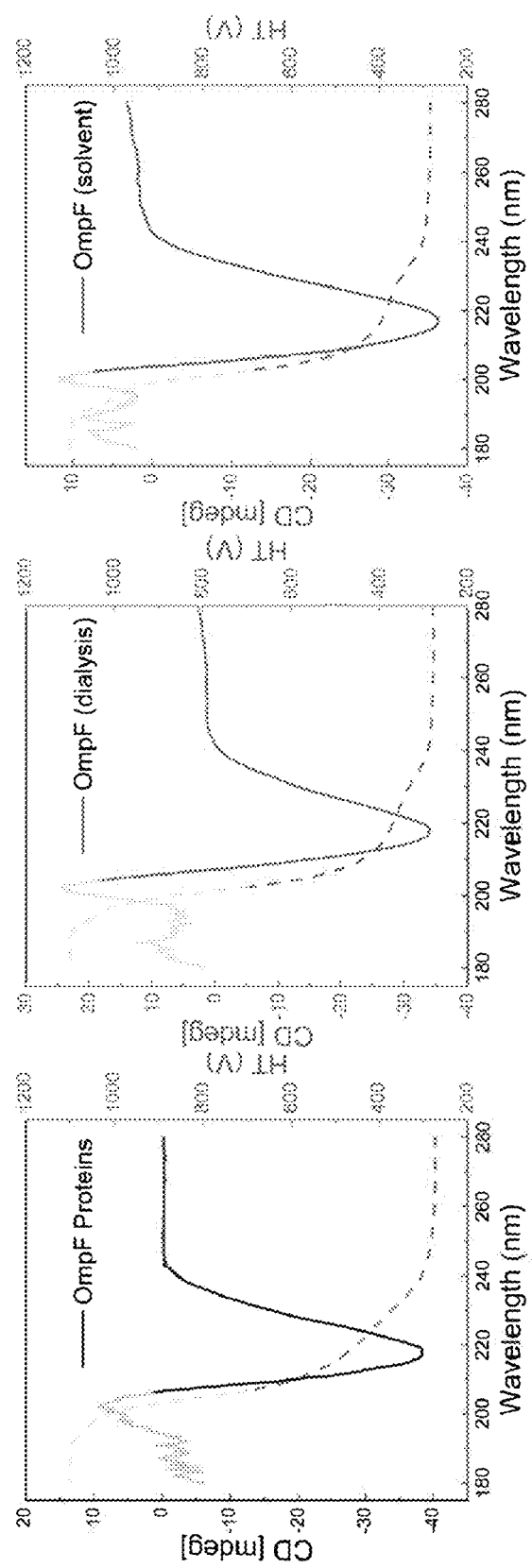
FIG. 6 depicts the strong absorption effect of rehydration buffer at shorter wavelengths. If the high tension (HT) voltage is above 700 V, there are not enough photons being detected by the photomultiplier tube (PMT) to measure a reliable CD signal and the data points should not be considered.

Integrity of Pore-Forming β-Barrel Protein Structures in Crystals Formed from the Membrane Protein-BCP-MeOH/CHCl$_3$ Solvent Mixtures Preserving the structures of pore-forming β-barrel sheets, after processing in MeOH/CHCl$_3$ solvent mixtures was of critical importance, because denatured proteins may lose the unique pore structures that form the basis of this work. Circular dichroism (CD) spectroscopy was performed to confirm that the structural integrity of the three protein channels was retained after nanosheet formation via the solvent method process. Nanosheets formed by the more established dialysis method were also characterized for comparison. As shown in FIG. 4, the CD spectra of OmpF detergent-solubilized proteins revealed a positive peak near 200 nm and a negative peak around 220 nm, reflecting the predominantly β-sheet structure of the protein. For OmpF 2D crystals prepared by the dialysis and solvent method, similar representative peaks were observed near 220 nm, qualitatively suggesting that the β-barrel structure of OmpF was similarly maintained throughout both crystallization processes. Specifically, CD spectra peaks were shown to be red-shifted from purified proteins (216.8 nm), to crystals (dialysis method: 218.4 nm and solvent method: 220 nm). These shifts are expected due to the highly-aligned configurations of the β-barrel sheet structures within the 2D crystals. This phenomenon is also seen in the crystal structure of *E. coli* OmpF porins obtained in lipidic cubic phases (3POQ) (at 221 nm) (FIG. 4 and FIG. 5). This slight red shift of the peak position could be attributed to absorption flattening optical effects that are a consequence of the ordered distribution of peptides within a crystalline structure. The protein secondary structure content was estimated by fitting CD spectra with JWMVS-529 Multivariate SSE analysis program with 26 reference proteins. The structural content of OmpF (Table 1) indicates that β-sheet content of OmpF 2D crystals in BCPs increases compared to that of OmpF proteins in detergent and is close to that of lipidic cubic phase OmpF crystals (3POQ). This implies that OmpF 2D crystals not only preserve β-barrel structures after crystallization but also organize OmpF proteins into ordered and large aggregates in BCP membrane matrices. The peak position occurring at less than ~200 nm could not be characterized owing to the strong absorption at shorter wavelengths from the rehydration buffer (10 mM Tris, 1.2% OG, pH7.4) we used for crystallization (FIG. 6). As shown in FIG. 4, the secondary structure analysis of FhuA ΔC/Δ4L and αHL CD spectra also provides confidence that nanosheet assembly by both solvent and dialysis method can conserve β-sheet structures similarly. The secondary structure of FhuA ΔC/Δ4L-BCP and αHL-BCP nanosheets prepared by solvent and dialysis method showed higher percentage of β-sheet content than that of FhuA ΔC/Δ4L and αHL in detergent micelles, indicating a high packing density of proteins in BCP membrane matrix. Table 1 shows the calculated secondary structure contents and representative peak position of CD spectra.

TABLE 1

| β-Barrel Channel Protein | α-Helix | β-Sheet | β-Turn | Random | Peak position (nm) |
|---|---|---|---|---|---|
| OmpF | 0.19 | 0.34 | 0.10 | 0.36 | 216.8 |
| OmpF crystal (Dialysis) | 0.10 | 0.43 | 0.10 | 0.36 | 218.4 |
| OmpF crystal (Solvent) | 0.11 | 0.39 | 0.11 | 0.39 | 220 |
| OmpF, 3POU | 0.03 | 0.58 | | 0.39 | 221.0 |
| FhuA ΔC/ΔL | 0.23 | 0.28 | 0.14 | 0.35 | — |
| FhuA crystal (dialysis) | 0.09 | 0.41 | 0.12 | 0.38 | — |
| FhuA crystal (solvent) | 0.06 | 0.42 | 0.12 | 0.40 | — |
| αHL protein | 0.16 | 0.40 | 0.10 | 0.34 | 215.4 |
| αHL crystal (dialysis) | 0.18 | 0.35 | 0.12 | 0.36 | 214.2 |
| αHL crystal (solvent) | 0.02 | 0.48 | 0.10 | 0.40 | 216.2 |
| αHL, 7AHL | 0.04 | 0.58 | | 0.38 | 220.6 |

Membrane Performance of β-Barrel Channel Protein-BCPs Biomimetic Membranes

Figure 1C:
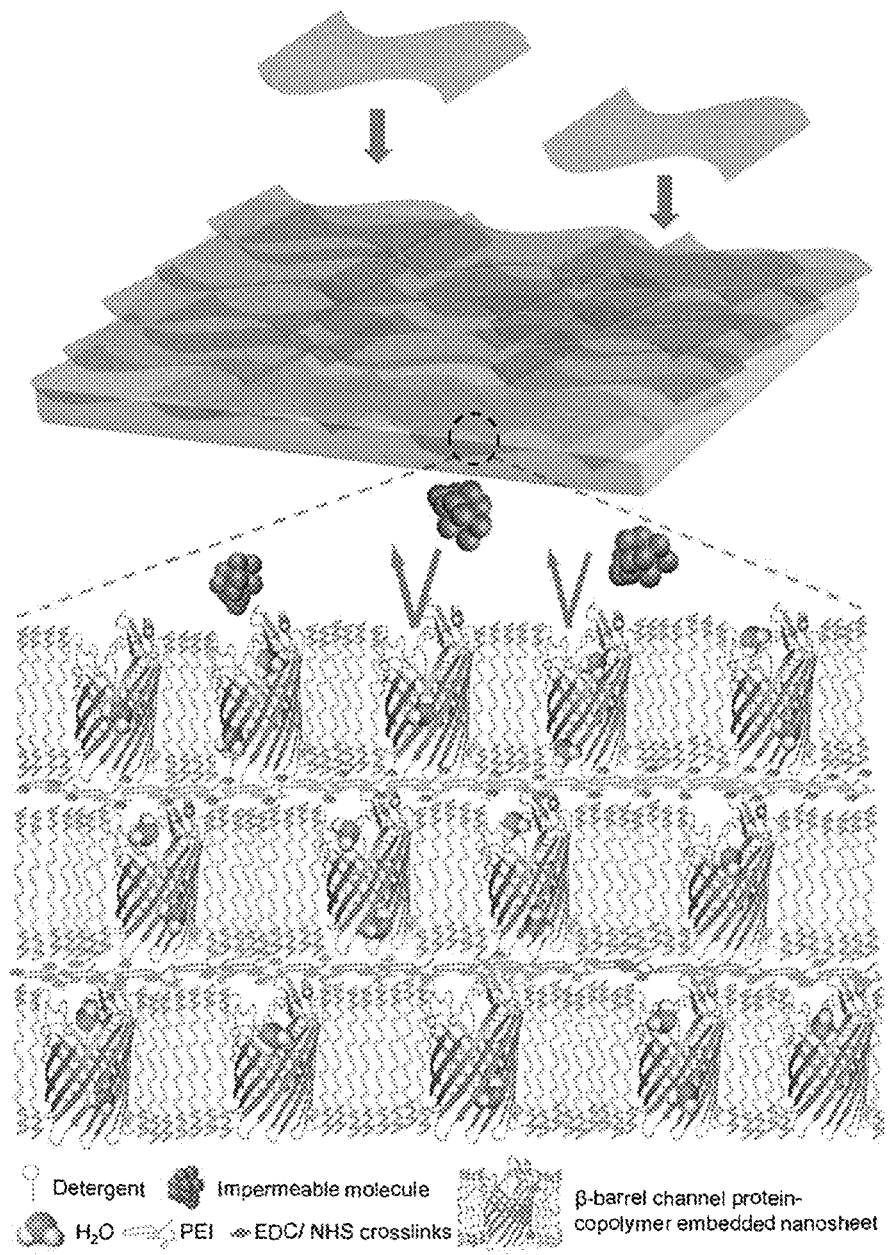

The formation of thin selective layers created through the deposition of 2D nanosheets on porous support membranes has been demonstrated recently for graphene oxide sheets and metal-organic frameworks nanosheets. Recently, we developed a modified layer-by-layer deposition technique to fabricate artificial water channel-based membranes from 2D sheets of polymer-channel composites. This method was adapted for membrane fabrication here (FIG. 1C).

Figure 7A:
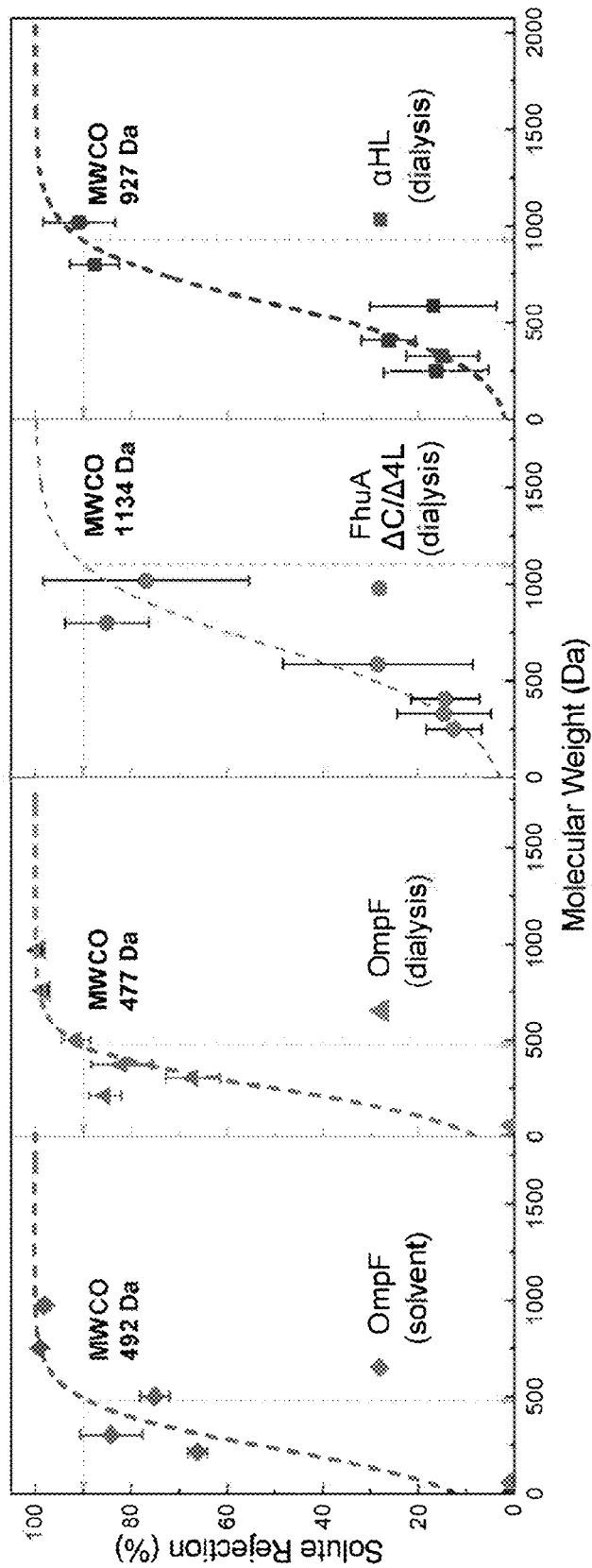
FIGS. 7A-C show that three β-barrel channel protein-copolymer based scalable membranes demonstrate distinct molecular separations and enhanced pure water permeability compared with current commercial membranes.
Figure 8A:
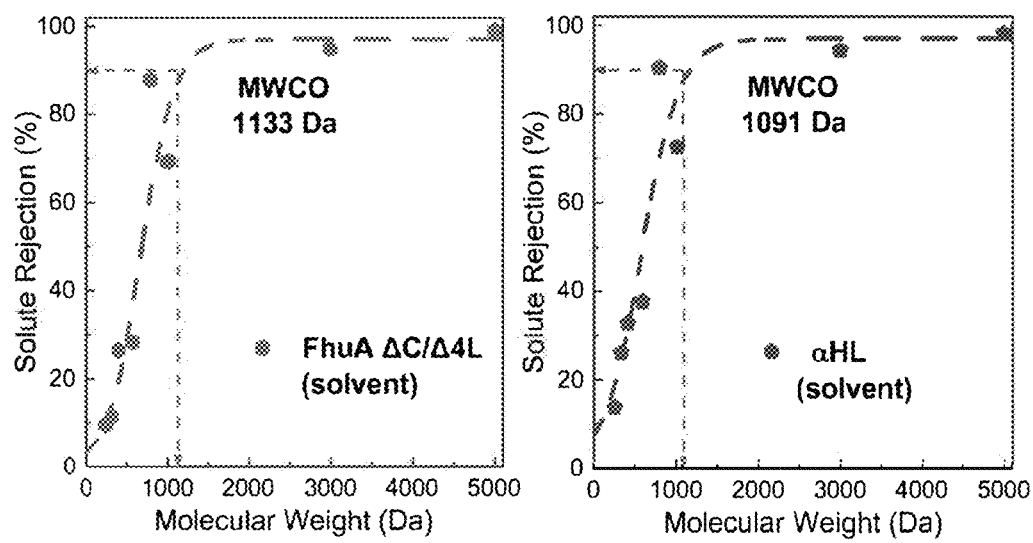
FIGS. 8A-B show solvent method driven αHL and FhuA ΔC/Δ4L 2D nanosheet-embedded biomimetic membranes also demonstrate specific solute rejection and high pure water permeability.

Membrane performance was characterized by measuring water permeation rates and solute rejection for a series of small molecular weight dyes in a dead-end filtration setup. The three β-barrel channel protein-embedded membranes exhibited unique small molecule separation performance with high water permeation rates compared to current commercial membranes. The MWCOs of these membranes were characterized by reporting the MW of the solute that was rejected at 90% under standard operating conditions. The rejection properties of OmpF 2D nanosheet-embedded membranes reached the expected MWCO as more nanosheet layers were deposited. Specifically, the MWCOs of membranes with 6-layers of nanosheets deposited were ~470 Da and ~500 Da for membranes with nanosheets prepared by the dialysis method and the solvent method, respectively. These values are close to the exclusion limit of native OmpF proteins of ~500-600 Da, determined using an in vitro vesicle reconstitution approach with radioactive hydrophilic solutes. These results demonstrate that OmpF 2D crystal-embedded selective layers were successfully fabricated on a porous PES support and maintained their expected transport performance. Additionally, the performances of the OmpF crystal-membranes formed with dialysis and solvent methods were nearly identical as discussed subsequently. The other two channel protein-based scalable membranes also manifest sharp and unique exclusion limits of ~920 Da and ~1100 Da for αHL (dialysis) and FhuA ΔC/Δ4L (dialysis) membranes, respectively (FIG. 7A). Membranes with 2D sheets created using the solvent method exhibit similar MWCOs (FIG. 8A). These molecular exclusion limits also confirm that channel proteins conserve their specific pore geometries in BCP membrane matrices with previously proposed MWCO of less than 2,000 Da for FhuA ΔC/Δ4L by poly(ethylene glycol)s (PEGs) partitioning and transport in a patch clamp set up as well as the region of 1,000 to 4,000 Da for αHL.

The small molecular weight dyes used for rejection tests are shown in Table 2. Note that the mass transfer coefficient (k) was determined from Colton-Smith empirical correlation and diffusivity (D) was calculated by the Stokes-Einstein equation. These values were used to correct apparent rejection based on the stagnant film model.

TABLE 2

| Dye | MW (Da) | k (m s$^{-1}$) | D (m$^2$ s$^{-1}$) |
|---|---|---|---|
| Chrysoidine G | 212.26 | 4.7 × 10$^{-5}$ | 6.2 × 10$^{-10}$ |
| Methyl orange | 304.02 | 4.3 × 10$^{-5}$ | 5.5 × 10$^{-10}$ |
| Crystal violet | 372.55 | 4.2 × 10$^{-5}$ | 5.2 × 10$^{-10}$ |
| Rhodamine B isothiocyanate | 500.63 | 3.9 × 10$^{-5}$ | 4.7 × 10$^{-10}$ |
| Acid fuchsin | 539.04 | 3.8 × 10$^{-5}$ | 4.6 × 10$^{-10}$ |
| Methyl blue | 753.84 | 3.5 × 10$^{-5}$ | 4.1 × 10$^{-10}$ |
| Rose bengal | 971.68 | 3.4 × 10$^{-5}$ | 3.8 × 10$^{-10}$ |
| Fluorescent dextran | 3000 | 2.6 × 10$^{-5}$ | 2.6 × 10$^{-10}$ |
| Blue dextran | 5000 | 2.3 × 10$^{-5}$ | 2.2 × 10$^{-10}$ |

Figure 7B:
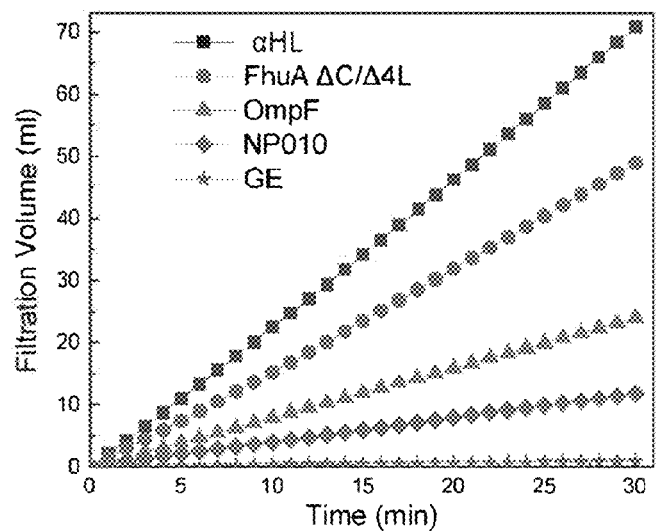

In addition to demonstrating tailored selectivity consistent with the channel protein pore size, the three channel protein-embedded membranes also demonstrated rapid and stable water permeation with applied pressure of 5 psi. Comparatively, commercial membranes with similar MWCOs of ~1,000 Da, NP010 (Microdyn Nadir™) and GE (Osmonics™ GE) had to be tested at an applied pressure of 50 psi to show appreciable flux (FIG. 7B).

Figure 7C:
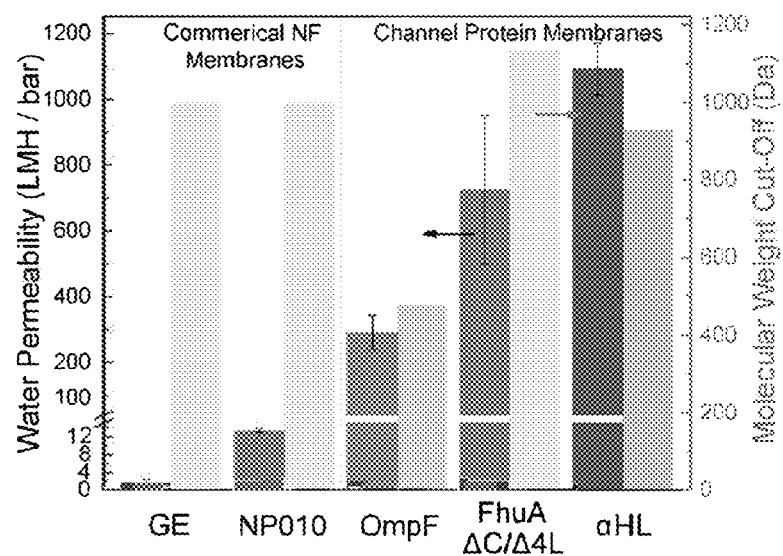
Figure 8B:
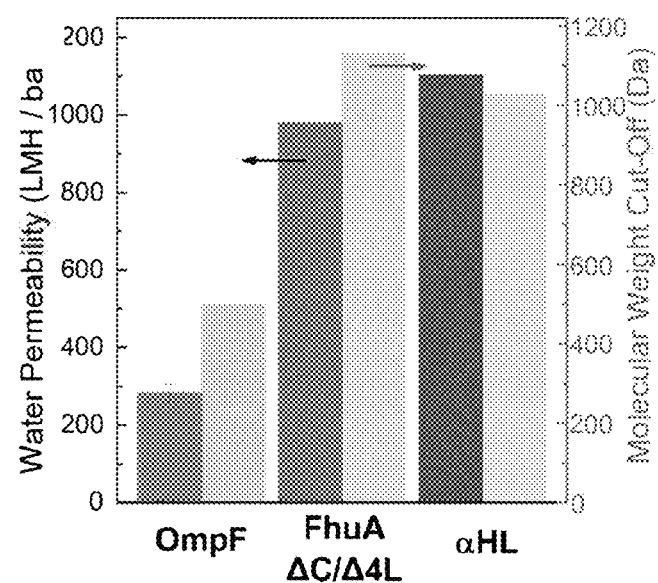

The water permeability of three β-barrel channel protein-embedded biomimetic membranes were ~293±51 LMH bar$^{-1}$ for OmpF (dialysis), 724.5±225.9 LMH bar$^{-1}$ for FhuA ΔC/Δ4L (dialysis), and 1,092±79.4 LMH bar$^{-1}$ for αHL (dialysis)-based scalable membranes (mean±s.d., n=3) (FIG. 7C). Membranes with 2D sheets created using the solvent method also demonstrated similar water permeabilities (FIG. 8B). These 6-layered protein composite membranes prepared using dialysis and solvent methods showed equivalent membrane performance in terms of separation properties (MWCO) and permeability indicating that the β-barrel pore structures and their function were preserved. These results recapitulate the advantages of solvent method over dialysis, especially from the perspective of process time and cost efficiency for membrane development.

The theoretical OmpF-membrane permeability was estimated at ~86.7 LMH bar$^{-1}$ based on OmpF single porin permeability, its channel packing density from hexagonal crystal structure, as well as PB-PEO block copolymer permeability. The remarkable agreement within a few folds between theoretical and experimental permeability, which were obtained from experiments spanning orders of magnitude length scales from the molecular scale to practice-relevant filtration scales, indicates successful integration of channel proteins into scalable membranes. The expected higher permeability of membranes constructed with the larger sized channels (FhuA and αHL) is also of the right scale when compared to the OmpF channels (their molecular permeability has not been characterized to the level that OmpF has been). The lower permeability for the higher pore size FhuA-based membrane compared to αHL may be a result of molecular interactions between water molecules and the pore wall which could have a higher impact than mere pore size at these nm length scales.

Membrane protein-based membranes exhibited orders of magnitude higher permeabilities relative to state-of-the-art polymeric NF membranes (FIG. 7C). For accurate comparison, two commercial membranes, NP010 and GE, which are rated to have MWCOs of ~1000 Da, were tested with the same experimental setup for their permeability values. Even though the commercial membranes had MWCO values similar to the value determined for the protein membranes, the water permeability of the control GE and NP010 membranes were 1.6±0.6 LMH bar$^{-1}$ and 13.2±0.5 LMH bar$^{-1}$, respectively compared to over ~300 LMH bar$^{-1}$ for all the membrane protein-based membranes tested in this study.

Figure 9:
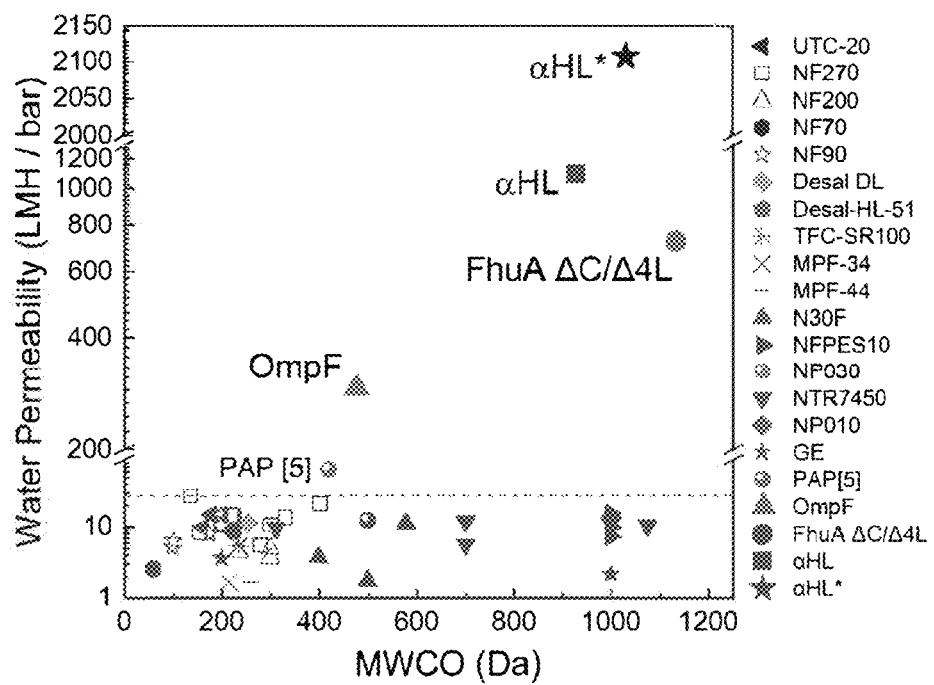
FIG. 9 shows a comparison of water permeability (LMH bar$^{-1}$) and MWCO (Da) of synthesized membranes with literature values on NF membranes reported in literature. The results clearly demonstrate that the β-barrel channel protein-based membranes have an order to almost three orders of magnitude higher permeability than commercial NF membranes with the MWCO ratings from 50 Da to 1,000 Da. αHL* represents composite membranes with αHL nanosheets supported on a highly permeable 0.03 μm PES support as compared to αHL indicating membranes supported on a lower permeability MP005 PES support used for all membranes. The dashed line (at a water permeability value of 27.5 LMH bar$^{-1}$) shows the upper limits of water permeability of current commercial membranes in the challenging sub nm to few nm separation range.

Extensive comparison of OmpF, αHL, and FhuA ΔC/Δ4L-based membranes to commercial membranes highlights significantly enhanced membrane performance of channel-based membranes (FIG. 9). Membrane protein channel-based membranes manifested ~20 to 1,000 folds enhanced water productivity over commercial membranes as a result of high pore packing densities of protein channels in the self-assembled 2D crystals and nanosheets. Specifically, the OmpF-membrane has ~25 times greater pure water permeability than the highest permeability commercial membrane, NP030 (water permeability of 14.1 LMH bar$^{-1}$ with MWCO of 500 Da) and ~100 times greater than N30F previously tested on the same experimental setup in our lab. In the separation range between 500 Da to 1,200 Da, αHL nanosheets supported on PES (Sterlitech Corp., WA) membrane demonstrates almost 1,000-fold water permeability of ~2000 LMH bar$^{-1}$ over the GE membrane (water permeability of 1.6±0.6 LMH bar$^{-1}$ with MWCO 1,000 Da).

Remarkably, OmpF-membranes show approximately an order of magnitude higher permeability than artificial channel based membranes of a similar MWCO (PAP[5] membranes, MWCO~500 Da). This corresponds to the tradeoff between expected two order higher single channel permeability of OmpF compared to PAP[5] channels and the one order lower effective cross sectional area of membrane proteins compared to artificial channels. These two opposing trend correspond to the one order increase in permeability of OmpF membranes compared to PAP[5] membranes created using a similar approach.

In summary, pore-forming membrane protein channels, OmpF, αHL and FhuA ΔC/Δ4L, were successfully integrated into membranes at close to practice-relevant centimeter size scales, along with development of a preparation method to create highly packed channel-nanosheets using a rapid organic solvent-based technique. Resulting biomimetic membranes demonstrated one to three orders of magnitude higher water permeability than commercial nanofiltration membranes with similar separation ratings while maintaining their expected high small solute selectivity.

Example 2: Aquaporin 2D Sample Preparation Using the Solvent Method

Figure 10A:
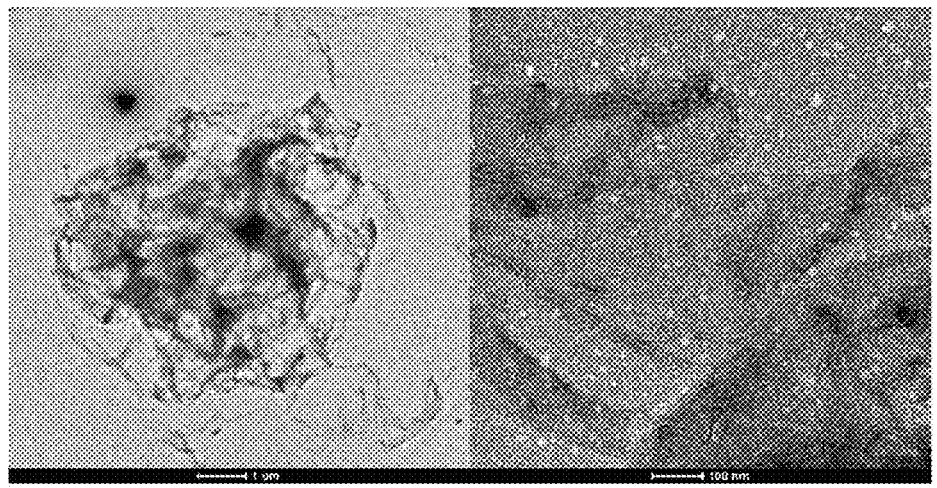
FIGS. 10A-B show TEM images of aquaporin 2D sheets prepared by the solvent method.
Figure 10B:
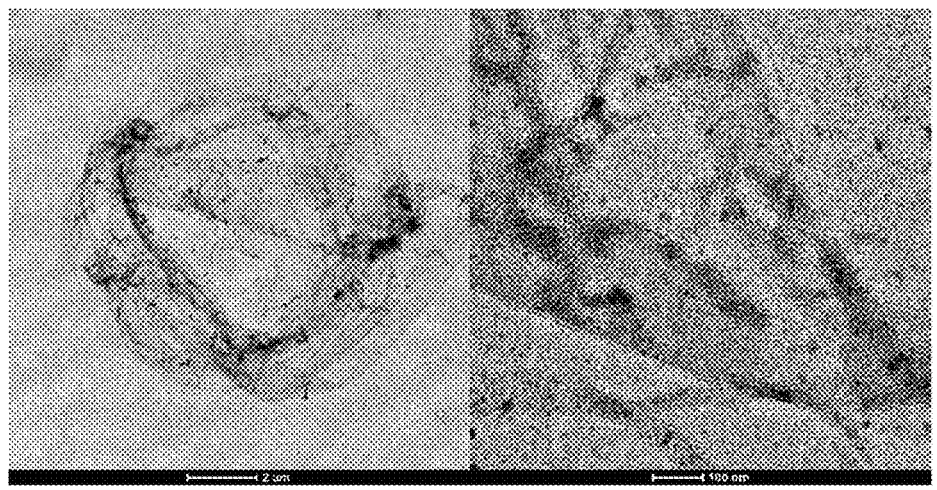

Aquaporin (AqpZ from *Rhodobacter sphaeroides*) 2D samples were prepared using the solvent method with different polymer to protein ratios (PoPr). Proteins precipitate during the solvent evaporation process for all three samples (PoPr 1:5, PoPr 1:3.3, and PoPr 1:2.5). TEM results showed no obvious 2D sheets for the PoPr 1:5 sample, while 2D sheets can be observed for both the PoPr 1:3.3 and PoPr 1:2.5 samples (FIG. 10). Also, protein aggregation can be observed for the PoPr 1:3.3 and PoPr 1:2.5 samples. The 2D sheet for the PoPr 1:3.3 and PoPr 1:2.5 samples were large sized (5-8 μm).

Figure 11:
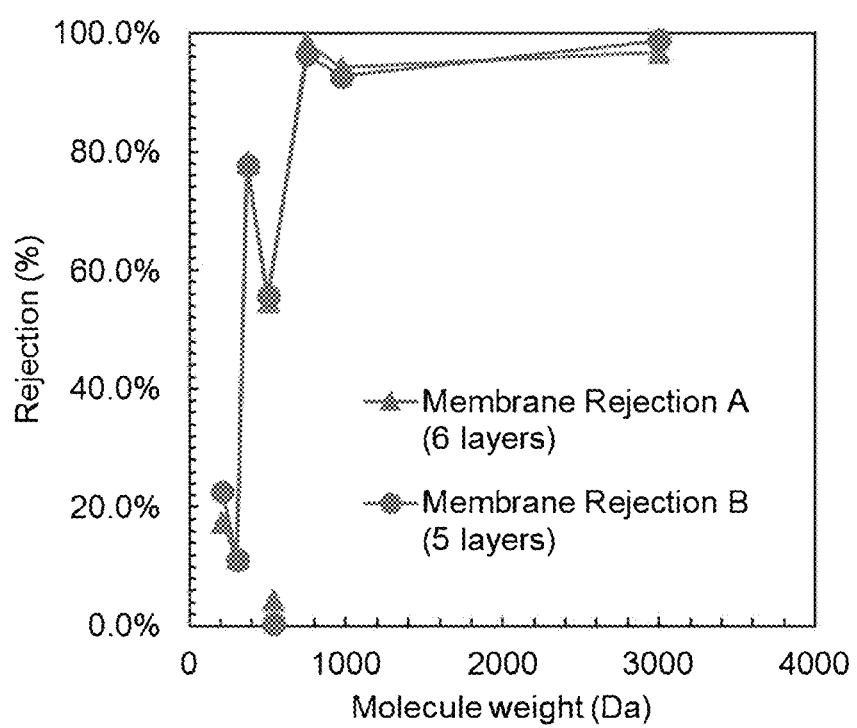
FIG. 11 shows the rejection results for dyes of various molecular weights with the RsAqpZ based membranes.

Both 5- and 6-layer RsAqpZ membranes (PES support) were utilized to test the filtration of various dyes. The results are shown in FIG. 11 and Tables 3 and 4. Note that the extremely low rejection of acid fuchsin may be caused by rhodamine B isothiocyanate remaining on the membrane and coming out during acid fuchsin filtration.

TABLE 3

| Dye | MW(Da) | Membrane A (6 layers) % Rejection | Membrane B (5 layers) % Rejection |
|---|---|---|---|
| Chrysoidine G | 212.26 | 17.4% | 22.6% |
| Methyl orange | 304.02 | 11.4% | 11.2% |
| Crystal violet | 372.55 | 78.2% | 77.7% |
| Rhodamine B isothiocyanate | 500.63 | 54.7% | 55.8% |
| Acid fuchsin | 539.04 | 4.4% | 0.4% |
| Methyl blue | 753.84 | 98.4% | 96.5% |
| Rose bengal | 971.68 | 94.3% | 92.7% |
| Fluorescent dextran | 3000 | 96.8% | 98.8% |

TABLE 4

| Dye | MW(Da) | Membrane A Flux (LMH/bar) | Membrane B Flux (LMH/bar) |
|---|---|---|---|
| Pure water | — | 269.8 | 286.6 |
| Chrysoidine G | 212.26 | 268.8 | 310.8 |
| Methyl orange | 304.02 | 302.2 | 355.4 |
| Crystal violet | 372.55 | 207.1 | 246.9 |
| Rhodamine B isothiocyanate | 500.63 | 150.1 | 182.5 |
| Acid fuchsin | 539.04 | 107.2 | 206.8 |
| Methyl blue | 753.84 | 210.9 | 253.8 |
| Rose bengal | 971.68 | 252.9 | 298.5 |
| Fluorescent dextran | 3000 | 236.0 | 286.2 |

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims. The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof

What is claimed is:
1. A nanosheet comprising:
   a block copolymer, an organic solvent, and a membrane protein comprising a pore or channel structure; wherein the pore or channel structure of the membrane protein is maintained in the nanosheet; wherein the nanosheet does not exhibit crystalline structure; wherein the organic solvent is selected from the group consisting of chloroform, decane, dodecane, heptane, hexane, methanol, or a mixture thereof; and wherein the block copolymer comprises one or more hydrophobic blocks and one or more hydrophilic blocks.
2. The nanosheet of claim 1, wherein the block copolymer comprises one or more hydrophobic blocks of polybutadiene (PB) and one or more hydrophilic blocks of polyethylene oxide (PEO).
3. The nanosheet of claim 1, wherein the pore or channel structure of the membrane protein has a diameter of from about 0.5 nm to about 1.5 nm.
4. The nanosheet of claim 1, wherein the membrane protein is a beta barrel membrane protein.

5. The nanosheet of claim 1, wherein the membrane protein is an alpha helical membrane protein.

6. The nanosheet of claim 1, wherein the membrane protein is a porin, a pore-forming toxin, or an aquaporin.

7. The nanosheet of claim 1, wherein the membrane protein is outer membrane protein F (OmpF), α-hemolysin toxin (αHL), ferrichrome outer membrane transporter (FhuA), or aquaporin Z (AqpZ).

8. The nanosheet of claim 1, wherein the membrane protein comprises one or more mutations to improve its thermal and/or solvent stability.

9. The nanosheet of claim 1, wherein the polymer and membrane protein are in a mass ratio of between about 10:1 and about 1:10.

10. The nanosheet of claim 1, wherein the nanosheet is attached to a substrate.

11. The nanosheet of claim 10, wherein the substrate comprises glass, plastic, composite, metal, or a mixture or combination thereof.

12. A membrane comprising:
    at least one nanosheet of claim 1 and one or more layers of an additional nanosheet and/or 2D crystal.

13. The membrane of claim 12, wherein the block copolymer comprises one or more hydrophobic blocks of polybutadiene (PB) and one or more hydrophilic blocks of polyethylene oxide (PEO).

14. The membrane of claim 12, wherein the pore or channel structure of the membrane protein has a diameter of from about 0.5 nm to about 1.5 nm.

15. The membrane of claim 12, wherein the membrane protein is a beta barrel membrane protein or an alpha helical membrane protein.

16. The membrane of claim 12, wherein the membrane protein is a porin, a pore-forming toxin, or an aquaporin.

17. The membrane of claim 12, wherein the membrane protein is outer membrane protein F (OmpF), α-hemolysin toxin (αHL), ferrichrome outer membrane transporter (FhuA), or aquaporin Z (AqpZ).

* * * * *